United States Patent
Rogers et al.

(10) Patent No.: US 12,383,174 B2
(45) Date of Patent: Aug. 12, 2025

(54) NON-VENTING BODILY FLUID SAMPLE OPTIMIZATION DEVICE AND SYSTEM

(71) Applicant: Kurin, Inc., San Diego, CA (US)

(72) Inventors: Bobby E. Rogers, San Diego, CA (US); Kevin Nason, Chandler, AZ (US); David Karl Stroup, San Diego, CA (US); David G. Matsuura, Solana Beach, CA (US); Belinko K. Matsuura, Encinitas, CA (US)

(73) Assignee: Kurin, Inc., San Diego, CA (US)

( * ) Notice: Subject to any disclaimer, the term of this patent is extended or adjusted under 35 U.S.C. 154(b) by 933 days.

(21) Appl. No.: 16/838,017

(22) Filed: Apr. 1, 2020

(65) Prior Publication Data

US 2020/0305780 A1    Oct. 1, 2020

Related U.S. Application Data

(60) Provisional application No. 62/827,783, filed on Apr. 1, 2019.

(51) Int. Cl.
   *A61B 5/15*    (2006.01)

(52) U.S. Cl.
   CPC .. *A61B 5/150213* (2013.01); *A61B 5/150099* (2013.01); *A61B 5/150351* (2013.01); *A61B 5/150992* (2013.01)

(58) Field of Classification Search
   None
   See application file for complete search history.

(56) References Cited

U.S. PATENT DOCUMENTS

| 3,382,865 A | 5/1968 | Worrall, Jr. |
| 3,494,352 A | 2/1970 | Russo |

(Continued)

FOREIGN PATENT DOCUMENTS

| CA | 2993646 | 2/2017 |
| CN | 1717280 | 1/2006 |

(Continued)

OTHER PUBLICATIONS

"Membrane Definition & Meaning." Merriam-Webster, Merriam-Webster, Apr. 22, 2009, www.merriam-webster.com/dictionary/membrane. (Year: 2009).*

(Continued)

*Primary Examiner* — Jacqueline Cheng
*Assistant Examiner* — Jairo H Portillo
(74) *Attorney, Agent, or Firm* — Pillsbury Winthrop Shaw Pittman LLP

(57) ABSTRACT

A fluid sample optimization device for optimizing a fluid sample includes an inlet, an outlet, a sample path connected between the inlet and the outlet, and a contaminant containment reservoir connected between the inlet and the outlet. The contaminant containment reservoir includes an air permeable fluid resistor proximate the outlet, and is arranged to receive, when a pressure differential is applied between the inlet and the outlet, a first portion of the fluid sample to displace air therein through the air permeable fluid resistor and the outlet, such that upon receipt of the first portion of the fluid sample and containment of the contaminants in the contaminant containment reservoir, subsequent portions of the fluid sample can be conveyed by the sample path from the inlet to the outlet when subsequent pressure differentials are applied between the inlet and the outlet.

12 Claims, 16 Drawing Sheets

(56) References Cited

U.S. PATENT DOCUMENTS

| | | |
|---|---|---|
| 3,604,410 A | 9/1971 | Whitacre |
| 3,648,684 A | 3/1972 | Barnwell |
| 3,741,197 A | 6/1973 | Sanz |
| 3,817,240 A | 6/1974 | Ayres |
| 3,835,835 A | 9/1974 | Thompson |
| 3,848,579 A | 11/1974 | Villa |
| 3,848,581 A | 11/1974 | Cinqualbre |
| 3,859,998 A | 1/1975 | Thomas |
| 3,874,367 A | 4/1975 | Ayres |
| 3,886,930 A | 6/1975 | Ryan |
| 3,945,380 A | 3/1976 | Dabney |
| 4,056,101 A | 11/1977 | Geissler |
| 4,057,050 A | 11/1977 | Sarstedt |
| 4,106,497 A | 8/1978 | Percarpio |
| 4,150,089 A | 4/1979 | Linet |
| 4,154,229 A | 5/1979 | Nugent |
| 4,193,400 A | 3/1980 | Loveless |
| 4,207,870 A | 6/1980 | Eldridge |
| 4,257,416 A | 3/1981 | Prager |
| 4,349,035 A | 9/1982 | Thomas |
| 4,373,535 A | 2/1983 | Martell |
| 4,412,548 A | 11/1983 | Hoch |
| 4,416,290 A | 11/1983 | Lutkowski |
| 4,416,291 A | 11/1983 | Kaufman |
| 4,436,098 A | 3/1984 | Kaufman |
| 4,444,203 A | 4/1984 | Engelman |
| 4,673,386 A | 6/1987 | Gordon |
| 4,690,154 A | 9/1987 | Woodford |
| 4,813,433 A | 3/1989 | Downey |
| 4,904,240 A | 2/1990 | Hoover |
| 4,980,297 A | 12/1990 | Haynes |
| 5,045,185 A | 9/1991 | Ohnaka |
| 5,097,842 A | 3/1992 | Bonn |
| 5,100,394 A | 3/1992 | Dudar |
| 5,135,489 A | 8/1992 | Jepson |
| 5,147,329 A | 9/1992 | Brannon |
| 5,200,325 A | 4/1993 | Blatt |
| 5,222,502 A | 6/1993 | Kurose |
| 5,401,262 A | 3/1995 | Karwoski |
| 5,417,673 A | 5/1995 | Gordon |
| 5,431,811 A | 7/1995 | Tusini |
| 5,432,084 A | 7/1995 | Brubaker |
| 5,439,450 A | 8/1995 | Haedt |
| 5,518,005 A | 5/1996 | Brannon |
| 5,520,193 A | 5/1996 | Suzuki |
| 5,632,906 A | 5/1997 | Ishida |
| 5,691,486 A | 11/1997 | Behringer |
| 5,749,857 A | 5/1998 | Cuppy |
| 5,772,608 A | 6/1998 | Dhas |
| 5,811,658 A | 9/1998 | Van Driel |
| 5,865,803 A | 2/1999 | Major |
| 5,873,841 A | 2/1999 | Brannon |
| 5,972,294 A | 10/1999 | Smith |
| 5,980,830 A | 11/1999 | Savage |
| 6,013,037 A | 1/2000 | Brannon |
| 6,106,509 A | 8/2000 | Loubser |
| 6,126,643 A | 10/2000 | Vaillancourt |
| 6,187,347 B1 | 2/2001 | Patterson |
| 6,224,561 B1 | 5/2001 | Swendson |
| 6,398,743 B1 | 6/2002 | Halseth |
| 6,506,182 B2 | 1/2003 | Estabrook |
| 6,569,117 B1 | 5/2003 | Ziv |
| 6,599,474 B2 | 7/2003 | Evtodienko |
| 6,626,884 B1 | 9/2003 | Dillon |
| 6,638,252 B2 | 10/2003 | Moulton |
| 6,695,004 B1 | 2/2004 | Raybuck |
| 6,733,433 B1 | 5/2004 | Fell |
| 6,736,783 B2 | 5/2004 | Blake |
| 6,843,775 B2 | 1/2005 | Hyun |
| 6,860,871 B2 | 3/2005 | Kuracina |
| 6,905,483 B2 | 6/2005 | Newby |
| 6,913,580 B2 | 7/2005 | Stone |
| 6,945,948 B2 | 9/2005 | Bainbridge |
| 7,052,603 B2 | 5/2006 | Schick |
| 7,055,401 B2 | 6/2006 | Prybella |
| 7,241,281 B2 | 7/2007 | Coelho |
| 7,306,736 B2 | 12/2007 | Collins |
| 7,461,671 B2 | 12/2008 | Ehwald |
| 7,479,131 B2 | 1/2009 | Mathias |
| 7,666,166 B1 | 2/2010 | Emmert |
| 8,070,725 B2 | 12/2011 | Christensen |
| 8,197,420 B2 | 6/2012 | Patton |
| 8,349,254 B2 | 1/2013 | Hoshino |
| 8,377,040 B2 | 2/2013 | Burkholz |
| 8,523,826 B2 | 9/2013 | Layton, Jr. |
| 8,535,241 B2 | 9/2013 | Bullington |
| 8,540,663 B2 | 9/2013 | Davey |
| 8,568,371 B2 | 10/2013 | Siopes |
| 8,574,203 B2 | 11/2013 | Stout |
| 8,603,009 B2 | 12/2013 | Tan |
| 8,827,958 B2 | 9/2014 | Bierman |
| 8,864,684 B2 | 10/2014 | Bullington |
| 9,022,950 B2 | 5/2015 | Bullington |
| 9,022,951 B2 | 5/2015 | Bullington |
| 9,060,724 B2 | 6/2015 | Bullington |
| 9,138,572 B2 | 9/2015 | Zeytoonian |
| 9,155,495 B2 | 10/2015 | Bullington |
| 9,204,864 B2 | 12/2015 | Bullington |
| 9,764,891 B1 | 9/2017 | Aviles |
| 9,820,682 B2 | 11/2017 | Rogers |
| 9,877,675 B2 | 1/2018 | Baid |
| 10,010,282 B2 | 7/2018 | Rogers |
| 10,143,412 B2 | 12/2018 | Rogers |
| 10,265,007 B2 | 4/2019 | Bullington |
| 10,299,713 B2 | 5/2019 | Patton |
| 10,596,315 B2 | 3/2020 | Bullington |
| 10,624,977 B2 | 4/2020 | Bullington |
| 10,827,964 B2 | 11/2020 | Rogers |
| 10,881,343 B2 | 1/2021 | Bullington |
| 11,185,266 B2 | 11/2021 | Rogers |
| 11,213,232 B2 | 1/2022 | Ivosevic |
| 11,234,626 B2 | 2/2022 | Bullington |
| 11,259,727 B2 | 3/2022 | Bullington |
| 11,311,219 B2 | 4/2022 | Rogers |
| 11,395,612 B2 | 7/2022 | Bullington |
| 11,419,531 B2 | 8/2022 | Bullington |
| 11,439,332 B2 | 9/2022 | Bullington |
| 11,589,843 B2 | 2/2023 | Bullington |
| 11,612,340 B2 | 3/2023 | Bullington |
| 11,653,863 B2 | 5/2023 | Bullington |
| 11,660,030 B2 | 5/2023 | Bullington |
| 11,737,693 B2 | 8/2023 | Bullington |
| 11,786,155 B2 | 10/2023 | Bullington |
| 11,789,017 B2 | 10/2023 | Bullington |
| 2001/0044615 A1 | 11/2001 | Amano |
| 2002/0004647 A1 | 1/2002 | Leong |
| 2003/0082074 A1 | 5/2003 | Jurik |
| 2003/0105414 A1 | 6/2003 | Leong |
| 2003/0185707 A1 | 10/2003 | Iwaki |
| 2003/0208151 A1 | 11/2003 | Kraus |
| 2004/0054333 A1 | 3/2004 | Theeuwes |
| 2004/0073171 A1 | 4/2004 | Rogers |
| 2004/0116830 A1 | 6/2004 | Trudeau |
| 2004/0147855 A1 | 7/2004 | Marsden |
| 2005/0004524 A1 | 1/2005 | Newby |
| 2005/0005635 A1 | 1/2005 | Le Metais |
| 2005/0007524 A1 | 1/2005 | Luo |
| 2005/0161112 A1 | 7/2005 | Ehwald |
| 2005/0240161 A1 | 10/2005 | Crawford |
| 2005/0245885 A1 | 11/2005 | Brown |
| 2005/0273019 A1 | 12/2005 | Conway |
| 2006/0009713 A1 | 1/2006 | Flaherty |
| 2007/0031283 A1* | 2/2007 | Davis ............ A61B 5/15087 422/400 |
| 2007/0083162 A1 | 4/2007 | Oreagan |
| 2007/0088279 A1 | 4/2007 | Shue |
| 2007/0119508 A1 | 5/2007 | West |
| 2008/0086085 A1 | 4/2008 | Brown |
| 2008/0145933 A1 | 6/2008 | Patton |
| 2008/0167577 A1 | 7/2008 | Weilbacher |
| 2008/0319346 A1 | 12/2008 | Crawford |
| 2009/0227953 A1 | 9/2009 | Tan |
| 2009/0299253 A1 | 12/2009 | Hursey |
| 2010/0010372 A1 | 1/2010 | Brown |

(56) References Cited

U.S. PATENT DOCUMENTS

| | | |
|---|---|---|
| 2010/0057004 A1 | 3/2010 | Christensen |
| 2011/0306899 A1 | 12/2011 | Brown |
| 2012/0016266 A1 | 1/2012 | Burkholz |
| 2013/0116599 A1 | 5/2013 | Bullington |
| 2013/0158506 A1 | 6/2013 | Harris |
| 2013/0317391 A1 | 11/2013 | Bullington |
| 2014/0039348 A1 | 2/2014 | Bullington |
| 2014/0107564 A1 | 4/2014 | Bullington |
| 2014/0112841 A1 | 4/2014 | Schoen et al. |
| 2014/0155781 A1 | 6/2014 | Bullington |
| 2014/0155782 A1 | 6/2014 | Bullington |
| 2014/0276578 A1 | 9/2014 | Bullington |
| 2015/0246352 A1 | 9/2015 | Bullington |
| 2015/0314105 A1 | 11/2015 | Gasparyan |
| 2015/0342510 A1 | 12/2015 | Bullington |
| 2015/0351678 A1 | 12/2015 | Bullington |
| 2015/0359473 A1 | 12/2015 | Garrett |
| 2016/0008579 A1 | 1/2016 | Burkholz |
| 2016/0017488 A1 | 1/2016 | Kobayashi |
| 2016/0073937 A1 | 3/2016 | Burkholz |
| 2016/0174888 A1 | 6/2016 | Berthier |
| 2016/0262677 A1 | 9/2016 | Ebetsberger |
| 2016/0325085 A1 | 11/2016 | Chelak |
| 2016/0361006 A1 | 12/2016 | Bullington |
| 2017/0020427 A1 | 1/2017 | Rogers |
| 2017/0020428 A1* | 1/2017 | Rogers .............. A61B 5/15003 |
| 2017/0065733 A1 | 3/2017 | Bullington |
| 2018/0140240 A1 | 5/2018 | Bullington |
| 2018/0177445 A1 | 6/2018 | Rogers |
| 2018/0271425 A1 | 9/2018 | Rogers et al. |
| 2018/0297303 A1 | 10/2018 | Sekiguchi |
| 2018/0353117 A1 | 12/2018 | Bullington |
| 2019/0159711 A1 | 5/2019 | Rogers |
| 2019/0175087 A1 | 6/2019 | Bullington |
| 2019/0365303 A1* | 12/2019 | Bullington ....... A61B 5/150213 |
| 2020/0289039 A1 | 9/2020 | Bullington |
| 2021/0145336 A1 | 5/2021 | Rogers |
| 2021/0275068 A1 | 9/2021 | Miazga |
| 2022/0151525 A1 | 5/2022 | Bullington |
| 2022/0151527 A1 | 5/2022 | Bullington |
| 2022/0160271 A1 | 5/2022 | Ivosevic |
| 2022/0304600 A1 | 9/2022 | Hammer |
| 2022/0304664 A1 | 9/2022 | Hammer |

FOREIGN PATENT DOCUMENTS

| | | |
|---|---|---|
| CN | 101352346 | 1/2009 |
| CN | 104107054 | 10/2014 |
| CN | 104981203 | 10/2015 |
| CN | 205127111 | 4/2016 |
| DE | 7203008 | 5/1972 |
| DE | 2541494 | 3/1977 |
| DE | 29913417 | 12/2000 |
| DE | 10038026 | 2/2001 |
| DE | 10134913 | 2/2003 |
| DE | 10134913 C2 | 6/2003 |
| DE | 10243129 | 4/2004 |
| EP | 0448795 A2 | 10/1991 |
| EP | 1665986 | 6/2006 |
| EP | 2593169 A1 | 5/2013 |
| EP | 3324845 A1 | 5/2018 |
| EP | 3562397 A1 | 11/2019 |
| EP | 3622890 A1 | 3/2020 |
| GB | 1378602 A | 12/1974 |
| JP | S5643474 | 10/1981 |
| JP | S5789869 | 6/1982 |
| JP | S5825146 | 2/1983 |
| JP | S5825146 A | 2/1983 |
| JP | S5867238 A | 4/1983 |
| JP | H02224742 | 9/1990 |
| JP | H08257018 | 10/1996 |
| JP | H09504726 A | 5/1997 |
| JP | 2001000424 | 1/2001 |
| JP | 2005349196 | 12/2005 |
| JP | 2009131273 A | 6/2009 |
| JP | 2012016496 A | 1/2012 |
| JP | 2013240628 | 12/2013 |
| JP | 5643474 | 12/2014 |
| JP | 5789869 B2 | 10/2015 |
| JP | 5825146 B2 | 12/2015 |
| JP | 5867238 B2 | 2/2016 |
| JP | 2016504075 | 2/2016 |
| JP | 2019534792 A | 12/2019 |
| JP | 2020000340 A | 1/2020 |
| JP | 6643474 B2 | 2/2020 |
| JP | 6734490 | 8/2020 |
| WO | 199216144 | 10/1992 |
| WO | 9605875 A1 | 2/1996 |
| WO | 1996005875 | 2/1996 |
| WO | 2007033319 A1 | 3/2007 |
| WO | 2008101025 | 8/2008 |
| WO | 2010062734 A1 | 6/2010 |
| WO | 2011162772 A1 | 12/2011 |
| WO | 2013082301 A1 | 6/2013 |
| WO | 2013181352 A1 | 12/2013 |
| WO | 2014058945 | 4/2014 |
| WO | 2015150742 | 10/2015 |
| WO | 2017019552 A1 | 2/2017 |
| WO | 2018125929 A1 | 7/2018 |
| WO | 2019055487 A1 | 3/2019 |
| WO | 2019232196 A1 | 12/2019 |

OTHER PUBLICATIONS

International Search Report and Written Opinion dated Jul. 16, 2020 for PCT application No. PCT/US2020/026276.
International Search Report and Written Opinion dated Nov. 5, 2015, for PCT application No. PCT/US2015/035870. 6 pages.
Bullington, et al., Systems and Methods for Sample Collection with Reduced Hemolysis, Exhibit H in U.S. Appl. No. 62/517,681, dated Jun. 9, 2017, 131 pages.
Communication Under Rule 71(3) EPC dated Apr. 22, 2020 for EP application No. 17840467.9. 125 pages.
European Patent Application No. EP19200766.4 extended European Search Report dated Dec. 2, 2019, 11 pages.
European Patent Office, Extended European Search Report for European Patent Application 20197213.0-1132, dated Dec. 9, 2020, 6 pages.
European Patent Office; Communication pursuant to Article 94(3) EPC; dated Oct. 31, 2018; 11 pages.
Examination Report No. 1 dated Apr. 29, 2020, for Australian Patent Application No. 2016297849. 3 pages.
International Search Report and Written Opinion dated Jun. 19, 2020, for PCT application No. PCTUS2020/023617. 12 pages.
European Patent Office, International Search Report and Written Opinion for PCT/US16/43709, dated Oct. 19, 2016, 14 pages.
International Search Report/Written Opinion for PCT/US17/68569 dated Apr. 25, 2018. 9 pages.
European Patent Office, International Search Report/Written Opinion for PCT/US17/068569 dated Apr. 25, 2018, 9 pages.
International Search Report and Written Opinion for PCT/US16/43709, Dated Oct. 19, 2016. 13 pages.
*Retractable Techs., Inc. v. Becton Dickinson & Co.*, CA No. 2:07-CV-250, Claim Construction Order (E.D. Tex., Jan. 20, 2009). 20 pages.
Hillyer, Christopher D., et al. "Bacterial Contamination of Blodd Components: Risks, Strategies and Regulation," Hematology, 2003, pp. 575-589.
De Korte, Dirk, et al. "Diversion of first blood volume results in a reduction of bacterial contamination for whole-blood collections." Vox sanguinis 83.1 (2002): 13-16.
Brecher, Mark E., et al. "Bacterial contamination of blood components." Clinical microbiology reviews 18.1 (2005): 195-204.
Van Zundert, Adrien. "New closed IV catheter system." Acta Anæsthesiologica Belgica 56.3 (2005): 283-285.
Hall, Keri K., et al. "Updated review of blood culture contamination." Clinical microbiology reviews 19.4 (2006): 788-802.
Li, Yiwen, et al. "Direct labeling and visualization of blood vessels with lipophilic carbocyanine dye Dil." Nature protocols 3.11 (2008): 1703-1708.

(56) References Cited

OTHER PUBLICATIONS

Page, Catherine, et al. "Blood conservation devices in critical care: a narrative review." Annals of intensive care 3 (2013): 1-6.
Abbott Point of Care, Cartridge and Test Information, Art: 714258-010; Rev. Date: Aug. 15, 16, 1-6 pages.
Zimmon, David S. et al. "Effect of portal venous blood flow diversion on portal pressure." The Journal of Clinical Investigation 65.6 (1980): 1388-1397.
Patton, Richard G., et al. "Innovation for reducing blood culture contamination: initial specimen diversion technique." Journal of clinical microbiology 48.12 (2010): 4501-4503.
Tang, Menglin, et al. "Closed blood conservation device for reducing catheter-related infections in children after cardiac surgery." Critical Care Nurse 34.5 (2014): 53-60.
Ernst, Dennis J. et al. "NCCLS simplifies the order of draw: a brief history." MLO: medical laboratory observer 36.5 (2004): 1-5 pages.
Gottlieb, T. "Hazards of bacterial contamination of blood products." Anaesthesia and intensive care 21.1 (1993): 20-23.
Norberg, Alonna, et al. "Contamination rates of blood cultures obtained by dedicated phlebotomy vs intravenous catheter." Jama 289.6 (2003): 726-729.
Quilici, Nathalie, et al. "Differential quantitative blood cultures in the diagnosis of catheter-related sepsis in intensive care units." Clinical infectious diseases 25.5 (1997): 1066-1070.
Napolitano, Marcello, et al. "Quality control of bacterial contamination of blood components: the feasibility of diversion system testing." Blood Transfus 2 (2004): 231-232.
De Korte, Dirk, et al. "Effects of skin disinfection method, deviation bag, and bacterial screening on clinical safety of platelet transfusions in the Netherlands." Transfusion 46.3 (2006): 476-485.
Liumbruno, Giancarlo Maria, et al. "Reduction of the risk of bacterial contamination of blood components through diversion of the first part of the donation of blood and blood components." Blood Transfusion 7.2 (2009): 86.
NCCLS. Procedures for the Collection of Diagnostic Blood Specimens by Venipuncture; Approved Standard—Fifth Edition. H3-A5, vol. 23, No. 32. Replaces H3-A4; vol. 18, No. 7. 1-52 pages. http://demo.nextlab.ir/Organization/Documents/CLSI-Standards/CLSI-H3-A5.aspx.
Challiner, A., et al. "Venous/arterial blood management protection system." Anaesthesia 47.2 (1992): 169-169.
Murphy, Michael F. "Better Blood Transfusion." Journal of the Intensive Care Society 4.3 (2003): 78-80.
Palavecino, Elizabeth L., et al. "Detecting bacterial contamination in platelet products." Clinical laboratory 52.9-10 (2006): 443-456.
Sheppard, Chelsea A., et al. "Bacterial contamination of platelets for transfusion: recent advances and issues." Laboratory Medicine 36.12 (2005): 767-770.
Shulman, Gerald. "Quality of processed blood for autotransfusion." Journal of Extracorporeal Technology 32.1 (2000): 11-19.
Weinbaum, Fredric I., et al. "Doing it right the first time: quality improvement and the contaminant blood culture." Journal of Clinical Microbiology 35.3 (1997): 563-565.
Weinstein, Melvin P. "Blood culture contamination: persisting problems and partial progress." Journal of clinical microbiology 41.6 (2003): 2275-2278.
Weinstein, Melvin P., et al. "The clinical significance of positive blood cultures in the 1990s: a prospective comprehensive evaluation of the microbiology, epidemiology, and outcome of bacteremia and fungemia in adults." Clinical Infectious Diseases 24.4 (1997): 584-602.
Weinstein, Melvin P. "Current blood culture methods and systems: clinical concepts, technology, and interpretation of results." Clinical infectious diseases 23.1 (1996): 40-46.
Closed IV, BD Saf-T-Intima. "Catheter System, Becton, Dickinson and Company, Brochure." Retrieved from the Internet (Aug. 23, 2019). 4 pages.
Perez, P., et al. "Multivariate analysis of determinants of bacterial contamination of whole-blood donations." Vox Sanguinis 82.2 (2002): 55-60.
McDonald, Carl P. "Interventions implemented to reduce the risk of transmission of bacteria by transfusion in the English National Blood Service." Transfusion Medicine and Hemotherapy 38.4 (2011): 255-258.
Lifesciences, Edwards. "Conservation. Safety. Simplicity. Edwards VAMP and VAMP Jr. Systems." (2002). 4 pages.
Sheppard, et al., Bacterial Contamination of Platelets for Transfusion: Recent Advances and Issues, Labmedicine, vol. 36, No. 12, Dec. 2005 ("Sheppard 2005").
BD Diagnostics, "Venous Blood Collection, BD Vacutainer Passive Shielding Blood Collection Needle" literature (2005) 2 pages.
Barnard, Dorothy R., et al. "Fibronectin (cold insoluble globulin) in the neonate," The Journal of Pediatrics, vol. 102, Issue 3, Mar. 1983, pp. 453-455.
Mayer, G.A. "A Method for the Reliable Determination of Clotting Time in Whole Blood," Canadian Medical Association Journal, Jun. 15, 1955, vol. 72, pp. 927-929.
Ziegler, R., et al. "Controlled Clinical Laboratory Comparison of Two Supplemented Aerobic and Anaerobic Media Used in Automated Blood Culture Systems to Detect Bloodstream Infections," Journal of Clinical Microbiology, Mar. 1998, p. 657-661.
Pall Medical, "Leukotrap Filtration Systems for Whole Blood Derived Platelets, Leukotrap RC PL and Leukotrap PL Systems" literature, (2005) 8 pages.
Meissner, George F., et al., "The Standard Clotting Time, A Method Based on the Use of Whole Venous Blood in Capillary Tubes," The American Journal of Clinical Pathology, vol. 39, No. 3., pp. 321-323, Mar. 1963.
European Patent Application No. EP23155927.9 extended European Search Report dated Jul. 26, 2023, 8 pages.
JP Notice of Allowance mailed Jun. 20, 2023; 6 pages.
Examination Report dated Sep. 28, 2023, for European Patent Application No. 22181212.6. 5 pages.
Office Action (Notice of Section 18) dated Dec. 20, 2023 for IL App No. 309380 (pp. 1-5).
JP Office Action mailed Feb. 27, 2024; 11 pages.
U.S. Appl. No. 62/845,767, May 9, 2019, Brewer Michael.
Office Action (Non-Final Rejection) dated Apr. 25, 2023 for U.S. Appl. No. 16/838,017 (pp. 1-20).
Office Action (Final Rejection) dated Jan. 29, 2024 for U.S. Appl. No. 16/838,017 (pp. 1-44).
Office Action (Advisory Action) dated Feb. 9, 2024 for U.S. Appl. No. 16/838,017 (pp. 1-6).
Office Action (Non-Final Rejection) dated Apr. 16, 2024 for U.S. Appl. No. 16/838,017 (pp. 1-19).
Office Action (Non-Final Rejection) dated May 21, 2024 for IL App. 286812 (pp. 1-3).
First Office Action (Non-Final Rejection) dated Jan. 16, 2024 for JP App. 2021-558648 (pp. 1-6).
First Office Action (Non-Final Rejection) dated Sep. 27, 2023 for CN App. 202080000666.0 (pp. 1-11).
Second Office Action (Non-Final Rejection dated Apr. 28, 2024 for CN App. 202080000666.0 (pp. 1-11).
European Patent Office, Extended European Search Report for European Patent Application 21818838.1-1122, dated Apr. 22, 2024, 11 pages.
Australian Patent Office, Examination Report No. 1 for for Australian Patent Application 2021202622, dated Mar. 18, 2022, 3 pages.
Office Action (Final Rejection) dated Aug. 25, 2023 for U.S. Appl. No. 18/113,710 (pp. 1-50).
European Patent Office, Extended European Search Report for European Patent Application 23155927.9-1122, dated Jul. 26, 2023, pp. 1-8.
Notice of Allowance mailed Apr. 17, 2024; 16 pages.
Office Action (Non-Final Rejection) mailed Oct. 4, 2023 for U.S. Appl. No. 17/538,900 (1-47).
First Office Action (Non-Final Rejection) dated Aug. 3, 2023 for CN Application No. 202010300942.7. 21 pages.
Office Action (Non-Final Rejection) dated Feb. 21, 2023 for U.S. Appl. No. 17/893,079, pp. 1-32.
Office Action (Final Rejection) dated Jul. 19, 2023 for U.S. Appl. No. 17/893,079, pp. 1-21.

(56) References Cited

OTHER PUBLICATIONS

Advisory Action dated Sep. 29, 2023 for U.S. Appl. No. 17/893,079, pp. 1-24.
European Patent Office, Examination Report for European Patent Application 22181212.6-1122, dated Sep. 28, 2023, pp. 1-5.
European Patent Office, Extended European Search Report for European Patent Application 20781928.5-1122 dated Oct. 28, 2022, pp. 1-10.
Rule 70(a) Communication for European Application No. 20781928.5-1122 dated Nov. 15, 2022, 1 page.
International Search Report and Written Opinion dated Mar. 19, 2020 for PCT application No. PCT/US2020/023617. pages.
International Search Report and Written Opinion dated Sep. 28, 2021 for PCT application No. PCT/ US2021/035294. 7 pages.
European Patent Office, Extended European Search Report for European Patent Application 22181212.6-1122 dated Oct. 24, 2022, pp. 1-10.
Australian Patent Office, Australian Examination Report No. 1 for Application No. 2021120 622 dated Mar. 18, 2022, 3 pages.
Notice of Allowance mailed Mar. 1, 2023; 3 pages.
First Office Action dated Nov. 24, 2021 for IL Application No. 286030, pp. 1-3.
Notice of Allowance mailed Jan. 29, 2023; 87 pages.
Office Action (Non-Final Rejection) dated Aug. 10, 2021 for Japanese Application No. 2020-118498, pp. 1-7.
Office Action (Non-Final Rejection) dated Mar. 28, 2022 for Japanese Application No. 2020-118498, pp. 1-3.
Office Action (Non-Final Rejection) dated Sep. 1, 2022 for Japanese Application No. 2020-118498, pp. 1-4.
Notice of Allowance mailed Apr. 4, 2023; 6 pages.
Rule 71(3) Communication and Text for Grant mailed Aug. 31, 2022 for European Application No. 19200766.4-1122. 189 pages.
Office Action (Non-Final Rejection) mailed Jan. 21, 2022 for Israeli Application No. 267684. 3 pages.
Notice of Allowance mailed Feb. 14, 2023; 122 pages.
Office Action (Non-Final Rejection) mailed Nov. 29, 2022 for Application No. 2021-214177, pp. 1-3.
Notice of Allowance mailed Jun. 20, 2023; 6 pages.
Office Action (Non-Final Rejection) mailed Nov. 4, 2022 for U.S. Appl. No. 17/094,692, pp. 1-50.
Notice of Allowance mailed Apr. 20, 2023; 36 pages.
Office Action (Non-Final Rejection) mailed Aug. 4, 2022 for U.S. Appl. No. 16/819,033, pp. 1-35.
Notice of Allowance mailed Nov. 28, 2022; 9 pages.
Office Action (Non-Final Rejection) mailed Apr. 16, 2024 for U.S. Appl. No. 16/838,017, pp. 1-35.
Second Office Action dated Apr. 28, 2024 for CN Application No. 202080000666.0, pp. 1-28.
Notice of Allowance mailed Jul. 4, 2024; 9 pages.
Office Action mailed May 21, 2024; 6 pages.
European Patent Office, Examination Report for European Patent Application 21818838.1, dated Apr. 22, 2024, pp. 1-11.
European Patent Office, Examination Report for European Patent Application 20781928.5, dated Jul. 31, 2024, pp. 1-6.
Notice of Allowance mailed Sep. 11, 2024; 6 pages.
Office Action (Grounds) mailed Mar. 11, 2025 for Application No. 2022-572789, pp. 1-11.
Office Action (Restriction Requirement) mailed Mar. 18, 2025 for U.S. Appl. No. 17/336,178, pp. 1-7.

\* cited by examiner

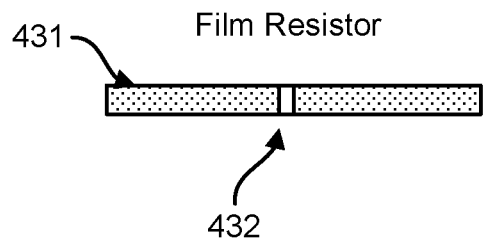
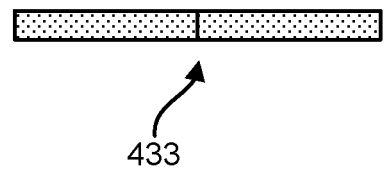
FIG. 6B      FIG. 6C
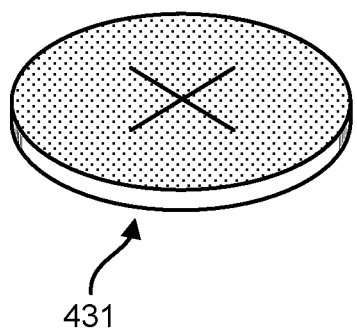
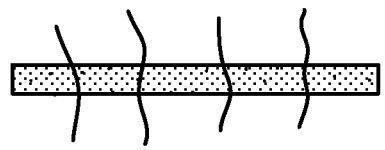
FIG. 6D      FIG. 6E
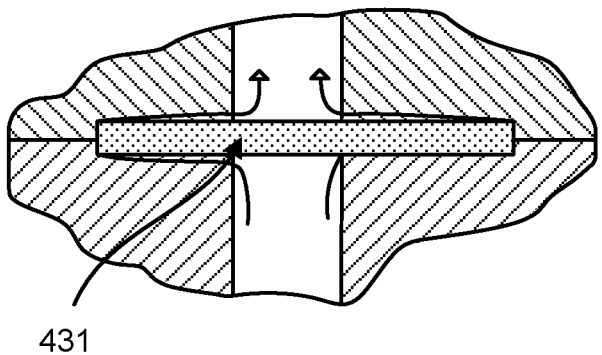
air leak path around film or plug
FIG. 6F Plug Resistor

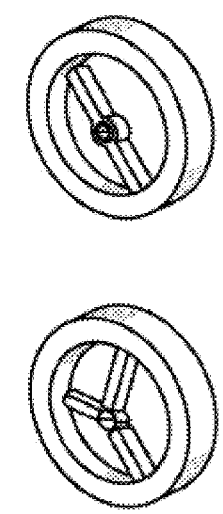
FIG. 9A
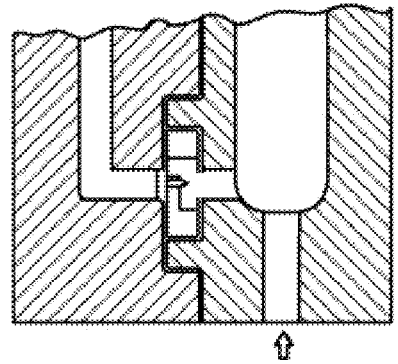
FIG. 9B
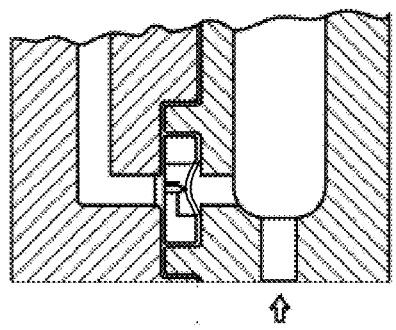
FIG. 9C
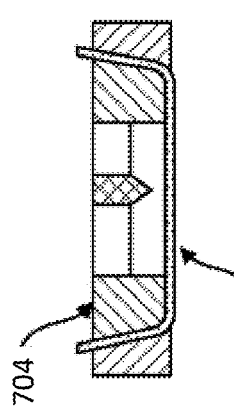
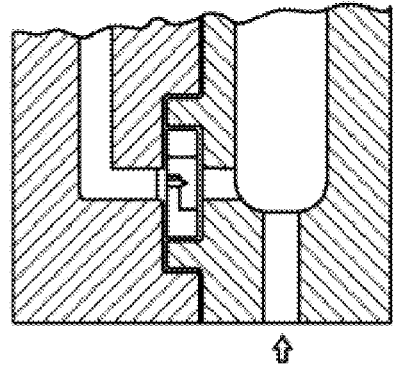

NON-VENTING BODILY FLUID SAMPLE OPTIMIZATION DEVICE AND SYSTEM

CROSS-REFERENCE TO RELATED APPLICATIONS

This application claims the benefit of U.S. Provisional Application No. 62/827,783, filed Apr. 1, 2019. This application is incorporated herein by reference in its entirety.

BACKGROUND

Bacteraemia is the presence of microorganisms in the blood. Sepsis, on the other hand, is bacteraemia in the presence of clinical symptoms and signs such as fever, tachycardia, tachypnea and hypotension. Bacteraemia and sepsis are associated with a high mortality and an increased incidence and duration of hospital stay and associated costs. Many bacteraemias, sepsis, fungaemias and other pathogens actually occur within a hospital or other healthcare settings with catheters and venipunctures being a source of contamination as potential carriers of these pathogens.

Blood cultures are the standard test used to detect microbial pathogens related to bacteraemia and sepsis in a patient's blood. The term blood culture refers to a single venipuncture, either from a peripheral site or central or arterial line, with the blood inoculated into one or more blood culture bottles or containers. One bottle is considered a blood culture where two or more are considered a set. Multiple sets may be obtained from multiple venipunctures and are associated with different sites on the patient.

These methods allow for microbial identification and susceptibility testing to be performed, which is a critical component to managing sepsis, however the lack of rapid results and decreased sensitivity for fastidious pathogens has led to the development of improved systems and adjunctive molecular or proteomic testing.

Collection of blood samples for conducting blood cultures is a critical component of modern patient care and can either positively affect the patient outcome by providing an accurate diagnosis, or can adversely affect the outcome by providing a false positive result of an infection, prolonging unnecessary antimicrobial therapy, the length of hospital stays, and increasing costs.

One outcome of collection of blood cultures is contamination. Blood culture contamination can lead to a false positive culture result and/or significant increase in healthcare related costs. Sources of blood culture contamination include improper skin antisepsis, improper collection tube disinfection, and contamination of an initial amount of blood of a blood draw, which may then skew results.

Blood culture collection kits generally consist of a "butterfly" set, infusion set, or other type of venipuncture device as offered by companies like BD, Smiths, B. Braun and others, and aerobic and anaerobic blood culture bottles. Various different bottles are also available depending on the test requirements. These bottles are specifically designed to optimize recovery of both aerobic and anaerobic organisms. In conventional kits, a bottle used is known generally as a "Vacutainer," which is a blood collection tube formed of a sterile glass or plastic tube with a closure that is evacuated to create a vacuum inside the tube to facilitate the draw of a predetermined volume of liquid such as blood.

False positive blood cultures are typically a result of poor sampling techniques. They cause the use of antibiotics when not needed, increasing hospital costs and patient anxiety. Blood cultures are drawn from a needlestick into the skin, and then a Vacutainer is attached to capture a sample of blood. Contamination may occur from improper or incomplete disinfection of the skin area in and around the puncture site. It may also occur from the coring of the skin by the needle during insertion, with the cored skin cells and any associated contamination being pulled into the sample.

Blood flow through a hypodermic needle is laminar, and as such, a velocity gradient can be developed across the flow tube as a pressure drop is applied to the hypodermic needle. Either forceful aspiration of blood, or using a very small hypodermic needle, can cause lysis and a release of potassium from the red blood cells, thereby potentially rendering the blood samples abnormal.

Various strategies have been implemented to decrease blood culture contamination rates, e.g. training staff with regard to aseptic collection technique, feedback with regard to contamination rates and implementation of blood culture collection kits. Although skin antisepsis can reduce the burden of contamination, 20% or more of skin organisms are located deep within the dermis and are unaffected by antisepsis. Changing needles before bottle inoculation is not advisable as it increases the risk to acquire needle stick injuries without decreasing contamination rates.

Some conventional systems and techniques for reducing blood culture contamination include discarding the initial aliquot of blood taken from central venous catheters, venipunctures, and other vascular access systems. However, these systems require the user to mechanically manipulate an intravascular device or require a complex series of steps that are difficult and reduce the chances they are consistently followed.

SUMMARY

This document describes a non-venting bodily fluid sample optimization device and system, for use in a blood sampling or blood culture collection system. In accordance with implementations described herein, a device has no moving parts, valves, state-transitioning switches or diverters, or other mechanisms that move, shift or transition from one operating mode to another operating mode, or from one state to another state.

In some implementations, a fluid sample optimization device includes an inlet port, an outlet port, and a contaminant containment reservoir having a proximal end coupled with the inlet port and a distal end coupled with the outlet port. The fluid sample optimization device further includes an air permeable fluid resistor positioned and secured within the contaminant containment reservoir, the air permeable fluid resistor having a front surface toward the proximal end of the contaminant containment reservoir and a rear surface toward the distal end of the contaminant containment reservoir. The fluid sample optimization device further includes a sample path having a proximal end connected with the inlet port near the proximal end of the contaminant containment reservoir, and a distal end coupled with the outlet port.

A drawing or pulling force applied to the outlet port, such as a vacuum pressure or the pulling of a plunger of a syringe, draws a first amount fluid such as venous blood into the inlet port and first into the contaminant containment reservoir, where air therein is pulled through the air permeable fluid resistor. Eventually, the fluid fills the contaminant containment reservoir and eventually encounters the air permeable fluid resistor, where it is at least partially trapped for at least a known period of time. Before the fluid can traverse and exit the air permeable fluid resistor, the force (such as a vacuum) draws a second amount of fluid into a parallel or co-existent sample path fluidically connected between the inlet port and the outlet port, to cause the second amount of fluid to bypass the contaminant containment reservoir and the fluid at least temporarily resistively maintained therein. Subsequent amounts of fluid to the second amount of fluid can also bypass the first amount of fluid and the contaminant containment reservoir, to be drawn into the inlet port through the sample path, and out the outlet port.

In some aspects, a fluid sample optimization device includes an inlet configured to connect with the fluid source, an outlet configured to connect with the fluid collection device, and a sample path connected between the inlet and the outlet. The fluid sample optimization device further includes a contaminant containment reservoir connected between the inlet and the outlet. One or more of the inlet, outlet, contaminant containment reservoir and sample path, and possibly other components of the fluid sample optimization device can be housed in and/or defined by a housing.

The contaminant containment reservoir further includes an air permeable fluid resistor connected with the sample path, preferably proximate the outlet. The contaminant containment reservoir is arranged to receive, when a pressure differential is applied between the inlet and the outlet, a first portion of the fluid sample from the fluid source to displace air therein through the air permeable fluid resistor and the outlet. The air permeable fluid resistor can be self-sealing upon contact with non-air fluid such as blood or other bodily fluids.

Upon receipt of the first portion of the fluid sample and containment of the contaminants in the contaminant containment reservoir, subsequent portions of the fluid sample can be received and conveyed by the sample path from the inlet to the outlet when subsequent pressure differentials are applied between the inlet and the outlet. In some implementations, the fluid sample optimization device includes a resistive plug that initially substantially plugs the sample path from the inlet while, and until, the first portion of the fluid is received in the contaminant containment reservoir.

In other aspects, a fluid sample optimization device for optimizing a fluid sample collected by a fluid collection device from a fluid source, where a first portion of the fluid sample potentially having contaminants, includes an inlet configured to connect with the fluid source and an outlet configured to connect with the fluid collection device. The fluid sample optimization device further includes a sample path connected between the inlet and the outlet. The sample path has a resistive plug that is configured to inhibit at least a part of the first portion of the fluid sample and the contaminants from entering the sample path.

The fluid sample optimization device further includes a contaminant containment reservoir connected between the inlet and the outlet. The contaminant containment reservoir has an air permeable fluid resistor proximate the outlet. The contaminant containment reservoir is arranged to receive, when a pressure differential is applied between the inlet and the outlet, the first portion of the fluid sample from the fluid source to displace air therein through the air permeable fluid resistor and the outlet, such that upon receipt of the first portion of the fluid sample and containment of the contaminants in the contaminant containment reservoir, subsequent portions of the fluid sample can be forced through the resistive plug of the sample path and conveyed by the sample path from the inlet to the outlet when subsequent pressure differentials are applied between the inlet and the outlet.

The details of one or more embodiments are set forth in the accompanying drawings and the description below. Other features and advantages will be apparent from the description and drawings, and from the claims.

BRIEF DESCRIPTION OF THE DRAWINGS

These and other aspects will now be described in detail with reference to the following drawings.

FIGS. 6A-6I shows an implementation of a non-venting fluid sample optimization device, as well as various implementations of a resistor;

FIGS. 9A-9C illustrate yet other implementations of a resistor having pierceable member;

Like reference symbols in the various drawings indicate like elements.

DETAILED DESCRIPTION

This document describes a fluid sample optimization device, for use in fluid sampling or fluid collection systems, such as for blood cultures or blood testing, or the like, and for containing contaminants that are likely in a first portion of a sampled or collected fluid. The fluid sample optimization device is configured for sequential fluid flows, i.e., to receive a first amount of bodily fluid from a patient, maintain at least a portion of the bodily fluid in a contaminant containment reservoir, and receive a second amount of bodily fluid from the patient via a sample path and automatically bypass the bodily fluid that is maintained in the contaminant containment reservoir. In some implementations, the bodily fluid is blood, and the first amount of blood can contain contaminants that might be picked up and mixed in with the first amount of blood by a venipuncture or other vascular access process, as an example.

Figure 1A:
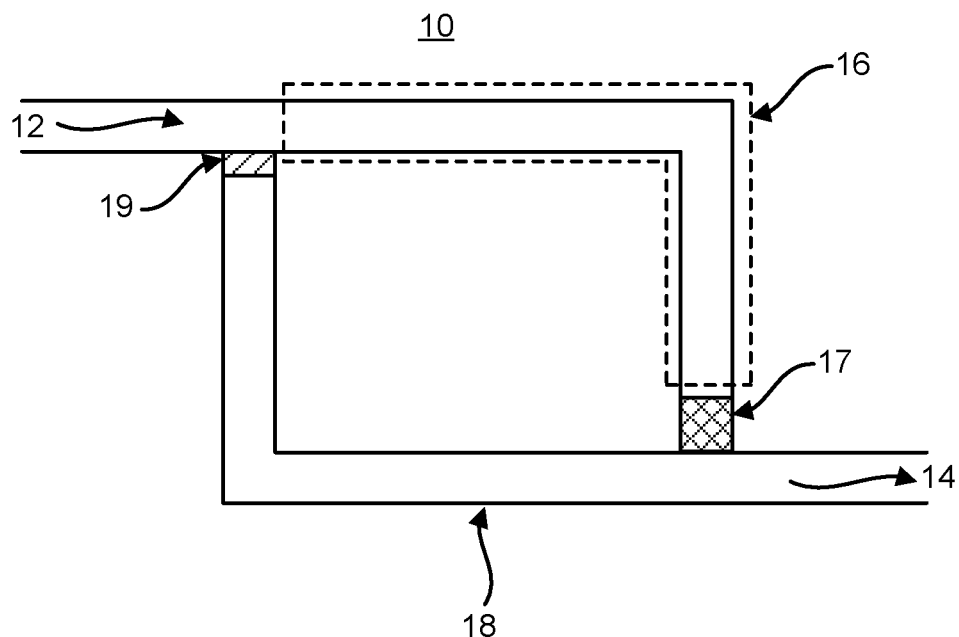
FIGS. 1A and 1B illustrate non-venting fluid contaminant sample optimization devices, in accordance with implementations described herein.

As illustrated in FIG. 1A, a fluid sample optimization device 10 includes an inlet 12 and an outlet 14. The inlet 12 can include an inlet port, connector or interface, for connecting to an external device such as tubing or interface thereof. The inlet 12 can be connected with a patient or a patient's fluid source, such as via a venipuncture needle, in which fluid is provided at pressure P1 and which can be the patient's own blood pressure. The outlet 14 can include an outlet port, connector or interface, for connecting to an external device such as tubing or an interface thereof. For instance, the outlet 14 can be connected with a fluid collection device, such as an evacuated tube like a Vacutainer® or a syringe, in which fluid is drawn by the fluid collection device from the fluid source by a pressure P2 that is lower than pressure P1. The differential pressure between P1 and P2 can allow the fluid sample optimization device 10 to be closed to atmosphere and atmospheric pressure, i.e. where the fluid sample optimization device 10 need not include any vent or pathway to outside atmosphere at least when in use.

The fluid sample optimization device 10 further includes a contaminant containment reservoir 16 connected with the inlet 12 and with the outlet 14, and having an air permeable fluid resistor 17 between a distal end of the contaminant containment reservoir 16 and the outlet 14. As further described herein, the contaminant containment reservoir 16 can be sized for holding a desired amount of fluid, and may contain an absorbent material that at least partially fills the contaminant containment reservoir 16. Also as further described herein, the contaminant containment reservoir 16 can be configured as a tortuous path, a series of chambers of differing cross sections and volumes, and/or contain rifling or baffles extending from an inner surface therein to minimize backflow, i.e. a flow toward the inlet 12.

The air permeable blood resistor 17 allows air to pass through and be displaced by a first portion or amount of fluid in the inlet 12 and sequestration chamber 16 when a pressure differential is applied between the inlet 12 and outlet 14, i.e. a negative pressure at the outlet 14 exceeds the pressure at the inlet 12. Once the fluid contacts the air permeable fluid resistor 17 the flow of fluid into the contaminant containment reservoir 16 is at least partially stopped, maintaining at least a portion of the fluid in the contaminant containment reservoir 16.

The fluid sample optimization device 10 further includes a sample path 18 also connected with the inlet 12 and the outlet 14. The sample path includes 18 a resistor 19 provided proximate the inlet 12. At the same time the pressure P2 is drawing the first portion or amount of fluid into the contaminant containment reservoir 16, the resistor 19 is configured to resist, inhibit, limit or prohibit a flow of the fluid into the sample path 18 until the first portion or amount of fluid has entered into the contaminant containment reservoir 16. As described further herein, the resistor 19 is configured such that after the first portion or amount of fluid has entered into the contaminant containment reservoir 16, the resistor 19 will allow a second and/or subsequent portions or amounts of fluid to flow from the inlet 12 through the sample path 18 to the outlet 14, still under force of the pressure differential between P2 and P1. Also as further described herein, the resistor 19 can be recessed in the sample path 18 away from the inlet 12, to allow for vacuum pressure to build up, and can also include a pilot hole or small capillary, aperture, iris, or the like, to allow the dissolvable material to initiate being dissolved by fluid that continues to be drawn toward the outlet 14.

As further described herein, the resistor 19 can be formed of a composition that includes at least portion of a dissolvable material. In specific implementations, the dissolvable material is dissolvable by contact with blood. Suitable materials for the dissolvable material can include, without limitation, any number of synthetic soluble polymers such as: polyvinal alcohol (PVA); polyvinylpyrrolidone (PVP), which is also commonly called polyvidone or povidone and is a water-soluble polymer made from the monomer N-vinylpyrrolidone; polyethylene glycol (PEG); polyethylene oxide (PEO); and/or other synthetic soluble polymers. Materials for the dissolvable material can also include, without limitation, any number of natural soluble polymers such as: hydroxypropelmethyl cellulose (HPMC), cellulose, corn starch or other starches, salt, and/or rice paper.

A key to the material used for the dissolvable material is that it must be inert or non-reactive to lab tests of sampled or collected fluid specimens, which are often provided with cultures to test for specific bacteria or viruses, or antibodies thereof, or other pathogens existing in the fluid sample. Stated another way, the dissolvable material should not include any substance or material that might materially affect a fluid sample test or determination. Further, such dissolvable material must be harmless to the patient in a very unlikely case of infusion by back-pressure or exposure to the patient's venous system.

Figure 1B:
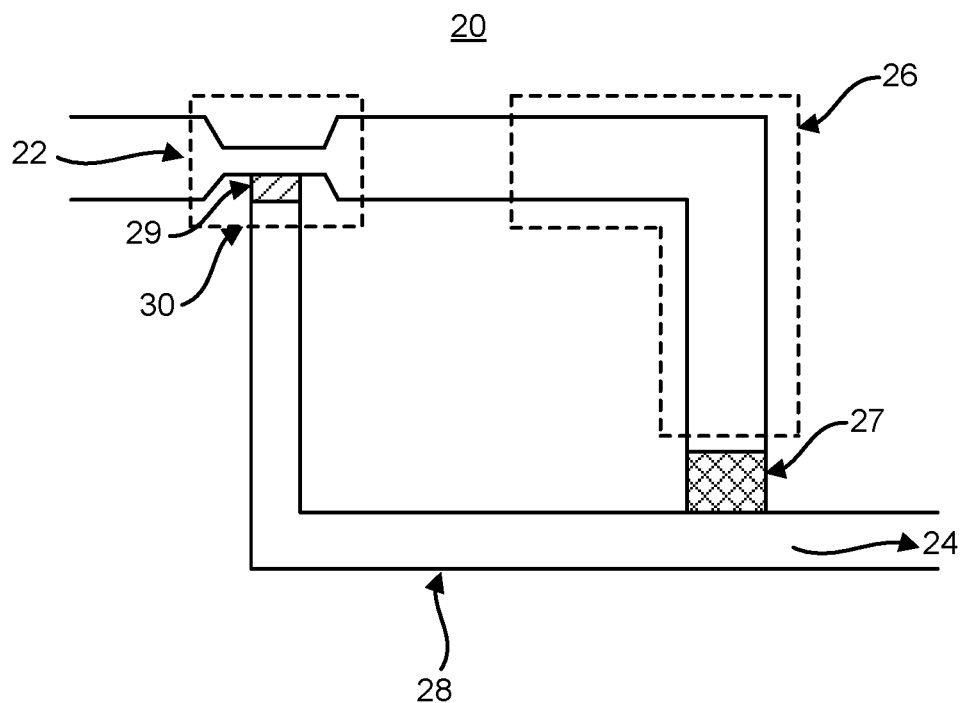

Consistent with FIG. 1A, FIG. 1B illustrates an implementation of a fluid sample optimization device 20 that includes an inlet 22 and an outlet 24. As described above, the inlet 22 can be connected with a patient or a patient's fluid source, such as via a venipuncture needle, in which fluid is provided at pressure P1 and which can be the patient's own blood pressure. The outlet 24 can be connected with a fluid collection device, such as an evacuated tube like a Vacutainer® or a syringe, in which fluid is drawn by the fluid collection device from the fluid source by a pressure P2 that is lower than pressure P1.

The fluid sample optimization device 20 further includes a contaminant containment reservoir 26 connected with the inlet 22 and with the outlet 24, and having an air permeable fluid resistor 27 between a distal end of the contaminant containment reservoir 26 and the outlet 24. The fluid sample optimization device 20 further includes a sample path 28 also connected with the inlet 22 and the outlet 24. The sample path includes 28 a resistor 29 provided proximate the inlet 22.

In some implementations, as illustrated in FIG. 1B, the fluid sample optimization device 20 can include an acceleration portion 30 to reduce fluid pressure of a fluid moving through it, and thereby increase a velocity of the fluid, such as from the inlet 22 to the contaminant containment reservoir 26. This can further help in preferentially directing the first portion or amount of fluid from the inlet 22 to the contaminant containment reservoir 26, before subsequent portions or amounts of fluid penetrate and traverse the resistor 29, to be output through the outlet 24 for collection. The acceleration portion can include a smaller cross sectional area, or constriction region, choke point or the like, such as in a Venturi path. The acceleration portion 30 can be followed by a larger cross-sectional area of the contaminant containment reservoir 26, which again, can be configured to hold a predetermined volume of fluid. In some implementations, the acceleration portion 30 can be positioned proximate to the connection point from the inlet 22 to the sample path 28, whereby once the contaminant containment reservoir 26 is filled, subsequent portions or amounts of blood will build up a pressure within the acceleration portion 30 in order to overcome resistor 29 to allow the subsequent portions or amounts to flow through the sample path 28 to the outlet 24.

Figure 2:
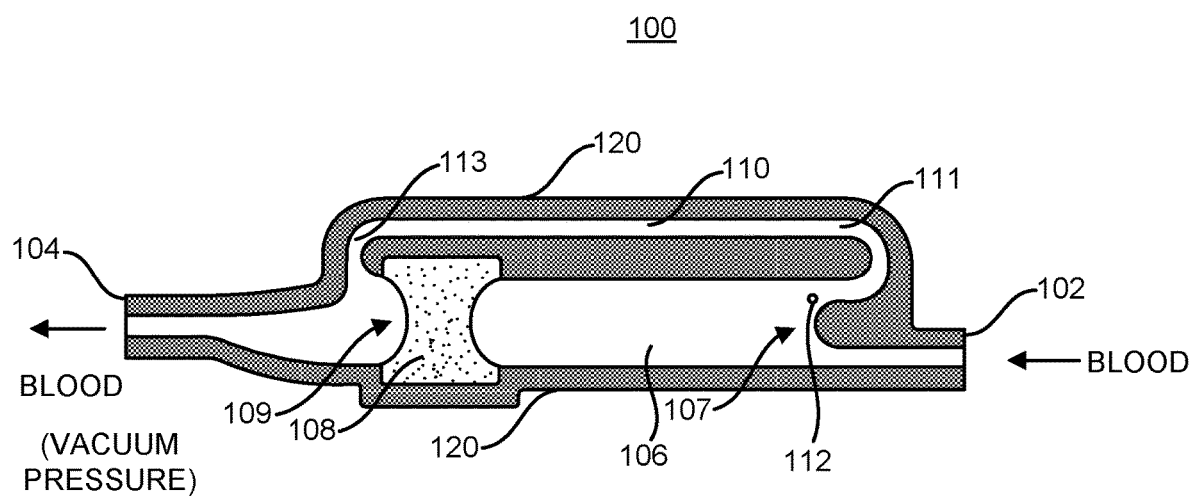
FIG. 2 shows a non-venting fluid contaminant sample optimization device, in accordance with implementations described herein.

FIG. 2 shows a fluid sample optimization device 100 that includes an inlet port 102 and an outlet port 104. The inlet port 102 can be fluidically coupled with a bodily fluid sample access device such as a patient needle, tubing, access port, catheter port or the like. The outlet port 104 can be fluidically coupled with a fluid collection device, such as a Vacutainer® set, which can include a sealed sampling needle on which a vacuum-sealed collection tube can be placed to break the seal and provide vacuum-based motive force through the fluid sample optimization device 100 from the inlet port 102 to the outlet port 104. The outlet port 104 can also be connected with any other collection device, such as a syringe, which may or may not use a plunger to create a pressure differential to "pull" fluid from a patient through the fluid sample optimization device 100.

The fluid sample optimization device 100 further includes a contaminant containment reservoir 106 having a proximal end 107 coupled with the inlet port 102 and a distal end 109 coupled, at least fluidically such as with air, with, or toward the outlet port 104. The contaminant containment reservoir 106 can have any shape and/or cross-sectional dimensions. Further, the transition from the inlet port 102 to the contaminant containment reservoir 106 can be straight or curved. In some implementations, the contaminant containment reservoir 106 is cylindrical or otherwise has a rounded cross-section, as smooth transitions with no sharp edges or corners can avoid hemolysis if the fluid traversing or bypassing the contaminant containment reservoir 106, is blood.

The fluid sample optimization device 100 further includes an air permeable fluid resistor 108 positioned and secured within the contaminant containment reservoir 106, and which is also referred to herein as a "plug." The air permeable fluid resistor 108 can be a complete or partial resistor to the passage of fluid therethrough, depending on time and pressure provided to the fluid. In accordance with some preferred implementations, the air permeable fluid resistor 108 has a front surface facing or toward the proximal end 107 of the contaminant containment reservoir 106, and a rear surface facing or toward the distal end 109 of the contaminant containment reservoir 106. The air permeable fluid resistor 108 allows passage of air from the contaminant containment reservoir 106, when a vacuum is applied to the outlet port 104 and as pushed by a first amount of bodily fluid, such as blood, through the air permeable fluid resistor 108 and toward and out the outlet port 104 of the fluid sample optimization device 100.

As with implementations described herein, the air permeable fluid resistor 108 can have a thickness or length of between less than 0.05 mm to up to 5 cm or more, and can be of a uniform or varying density. For instance, the air permeable fluid resistor 108 can be less dense and more porous on the side facing the proximal end 107 of the contaminant containment reservoir 106, and more dense and less porous toward the distal end 109 of the contaminant containment reservoir 106. The diameter of the air permeable fluid resistor 108 will match the internal dimensions of contaminant containment reservoir 106 in a manner that prevents blood from passing between the outer portion of air permeable fluid resistor 108 and the inner walls of contaminant containment reservoir 106. The air permeable fluid resistor 108 may also be in the form of multiple components constructed of diverse materials.

In some implementations, the air permeable fluid resistor 108 can be impregnated with a material that expands upon contact with a fluid such as blood. While shown in FIG. 2 as being positioned toward the distal end 109 of the contaminant containment reservoir 106, the air permeable fluid resistor 108 can be positioned anywhere along the length of the contaminant containment reservoir, and can extend from the proximal end 107 to the distal end 109, depending on how absorptive the material is that forms the air permeable fluid resistor 108. Filtration media that forms the air permeable fluid resistor 108 may be surface-modified, or additives may be incorporated into the porous matrix to enhance functionality depending on specific performance requirements, such as timing and/or fluid volumes, for example.

In some implementations, the air permeable fluid resistor 108 is formed of a material, or combination of materials, that are configured to allow air to pass, but which can get saturated with a portion of the first amount of bodily fluid. The air permeable fluid resistor 108 can be formed at least in part by a porous polymer or plastic, and/or a natural fiber material such as cotton, hemp, or the like. In some implementations, the air permeable fluid resistor 108 can be formed of two portions: a first portion that is permeable to air and mostly impermeable to fluid at the distal end (toward the outlet 104); and a second portion that contains an additive that seals upon contact with blood at the proximal end (toward the contaminant containment reservoir 106). This configuration can keep the additive from mixing with the fluid flowing through the sample path and out to a collection bottle or the like. The air permeable fluid resistor 108 can receive and trap at least a part of the first portion of fluid, to thereby trap any contaminants therein.

The fluid sample optimization device 100 further includes a sample path 110 having a proximal end 111 connected with the inlet port near the proximal end 107 of the contaminant containment reservoir 106, and a distal end 113 coupled with the outlet port 104. The sample path 110 can be formed as a channel, tubing, track, passage, portion, cavity, housing, encasement, or the like. The air permeable fluid resistor 108 is configured to hold the part of the first portion of fluid for a time period sufficient to allow a second portion of bodily fluid to bypass the contaminant containment reservoir 106 via the sample path 110. As shown in FIG. 2, the sample path 110 can traverse the fluid sample optimization device 100 substantially parallel to an orientation of the contaminant containment reservoir 106. In some implementations, a cross-sectional area of the contaminant containment reservoir 106 can be larger than a cross-sectional area of the sample path 110, which can aid in preferentially directing a first amount of fluid from the inlet port 102 into the contaminant containment reservoir 106.

The inlet port 102, the proximal end of the contaminant containment reservoir 106, and the proximal end of the sample path 110 together form a junction 112. The junction 112 can include a number of curved passageways, such as leading to the proximal end of the sample path, and which can be configured to facilitate a fluid flow first into the contaminant containment reservoir 106 and then to bypass the contaminant containment reservoir 106 and into and through the sample path 110. Importantly, as distinct from various prior art blood diversion or blood sample optimization devices, the junction 112 relies on passive fluidic control and includes no active switches, valves or other mechanically movable device to divert or switch a fluid flow.

In terms of fluid dynamics, the resistance to flow in the initial path (R1) must be less than the resistance to flow in the sample path (R2). As the contaminant containment reservoir fills resistance is increased as blood is prevented from moving through the air permeable resistor. Air flows easily through it but not blood. As R1 increases as some point the scales tip and R1 becomes greater than R2. At that point blood will flow into the sample path. R2 can be increased with variations applied to the length, diameter and to some extent geometry. R1 can be reduced by the same means or variations, and by managing air permeability of the plug, as described in further detail herein.

In some implementations, the fluid sample optimization device 100 includes a housing 120 that forms and provides one or more of the inlet port 102, outlet port 104, contaminant containment reservoir 106, and sample path 110. For instance, the housing 120 can be formed of a top member mated with a bottom member, where one or both of the top member and bottom member are formed with grooves, channels, pathways, areas, or other features to define and provide the one or more of the inlet port 102, outlet port 104, contaminant containment reservoir 106, and sample path 110. The housing 120 can be made of a sturdy, resilient material such as plastic (i.e. polycarbonateacrylic, PVC, ABS, etc.), a metal, or the like, and which can be sanitized before use so as to be used in a clean, sanitized state, free of microbes. The inlet port 102 and/or the outlet port 104 can further include or be outfitted with connectors, such as a Luer connector or threaded connection.

Figure 3:
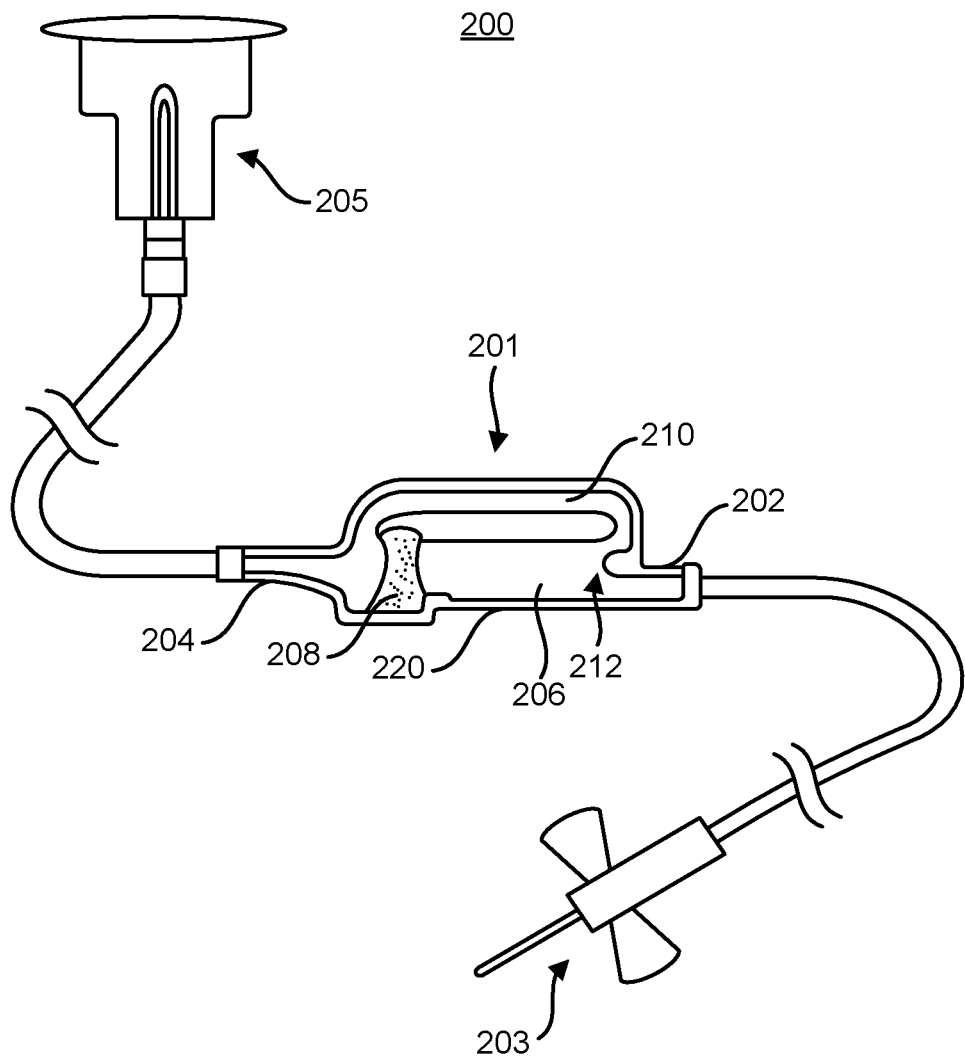
FIG. 3 shows a fluid sampling system using a fluid sample optimization device, in accordance with implementations described herein.

FIG. 3 illustrates a fluid sampling system 200, which includes a fluid sample optimization device 201 connected with a blood sampling pathway having a patient needle 203 and a sample collection device 205, which in some implementations includes an adapter with a sealed sample collection needle that receives one or more vacuum sample bottles. The patient needle 203 can be a safety-type vascular access needle, such as described in U.S. patent application Ser. No. 16/045,321, entitled "Needle Assembly with Needle Safety Shield," the contents of which are incorporated by reference herein for all purposes.

The fluid sample optimization device 201 includes an inlet port 202 connected with the patient needle 203, an outlet port 204 connected with the sample collection device 205, a contaminant containment reservoir 206 having an air permeable fluid resistor 208, and a sample path 210 having a proximal end fluidically coupled with the inlet port 202 and a distal end fluidically connected with the outlet port 204. The fluid sample optimization device 201 can further include a housing 220 that houses and defines one or more of the inlet port 202, the outlet port 204, the contaminant containment reservoir 206, and the sample path 210. The housing 220 can be formed of any rigid material that is susceptible to sterilization, or possibly having antimicrobial properties, but which can also shield the inlet port 202, outlet port 204, contaminant containment reservoir 206 and sample path 210, and any components therein, from external contamination.

Each of the contaminant containment reservoir 206 and the sample path 210 can be connected with the inlet port 202 via a junction 212 that is sized and configured to allow a first portion of fluid, such as blood, to be drawn, pulled, or otherwise flow, into the contaminant containment reservoir 206 to displace air therein through the air permeable fluid resistor 208, and for at least a portion to be maintained, at least temporarily, in the contaminant containment reservoir 206, and to allow a second portion of blood to bypass the contaminant containment reservoir 206 and flow into the sample path 210 toward the outlet port 204 and the sample collection device 205.

The sample collection device 205 can be a Vacutainer® type device, with a collection adapter having a collection needle that is sealed by an elastomeric seal that can be pierced by a vacuum-sealed collection bottle to expose the collection needle and allow insertion of the collection needle into a septum of the collection bottle. The vacuum in the collection bottle can be the force that helps draw the bodily fluid from a patient, through the fluid sample optimization device 201.

Figure 4A:
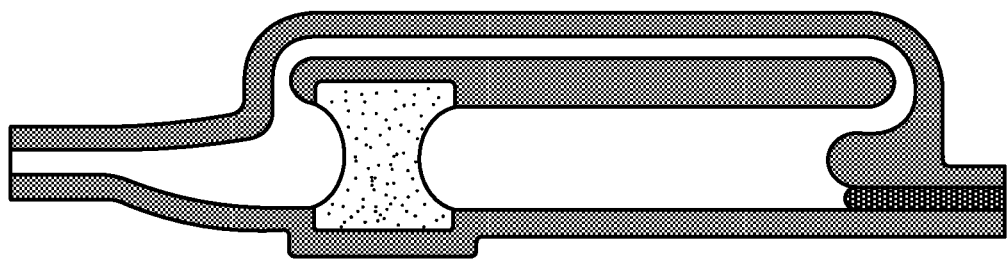
FIGS. 4A-4D illustrate a process for withdrawing a first amount of bodily fluid from a patient, and bypassing it to collect a second and/or subsequent amounts of bodily fluid.

FIGS. 4A-4D illustrate an operation of the fluid sample optimization device 100/201, and described specifically in the context of blood sampling, although other types of bodily fluids can be collected or sampled. With reference to FIG. 3, and as illustrated in FIG. 4A, when fluid collection device creates a low pressure at the outlet of the fluid sample optimization device, such as when a collection bottle or tube is inserted into a collection adapter, the pressure difference between the outlet and in inlet, such as by venipuncture of a patient (or more particularly, the patient's vascular blood pressure) will force the air out of the fluid sample optimization device and into the collection bottle, and blood will fill in behind it.

In the implementation shown, the air can flow through two parallel paths—through the plug in the contaminant containment reservoir and through the sample path. A volume of flow through each can be proportional to a resistance within each path. Accordingly, an optimal configuration for the fluid sample optimization device includes consideration of: volume of the contaminant containment reservoir, an arrangement of the junction connecting the inlet with the contaminant containment reservoir and the sample path, relative cross sectional dimensions of the inlet, contaminant containment reservoir, and sample path, a resistivity of the plug, a location and size of the plug, a curvature of various transitions or interfaces between the inlet, contaminant containment reservoir, and sample path, etc., and the like.

Figure 4B:
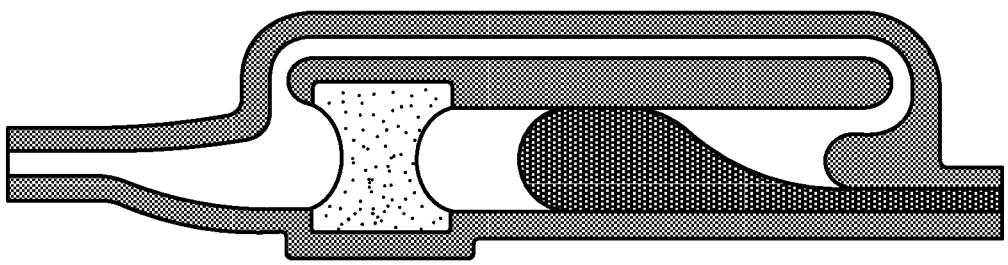
Figure 4C:
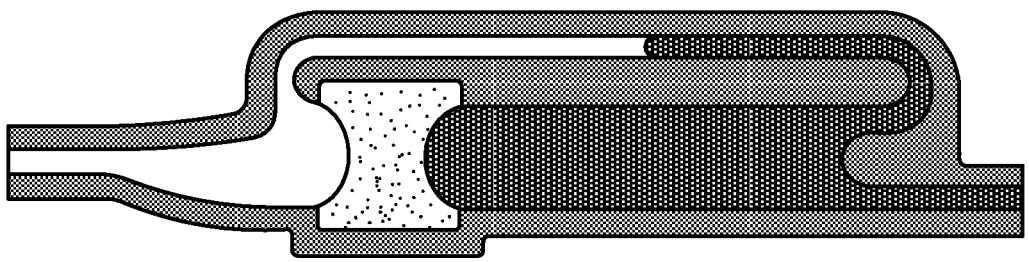
Figure 4D:
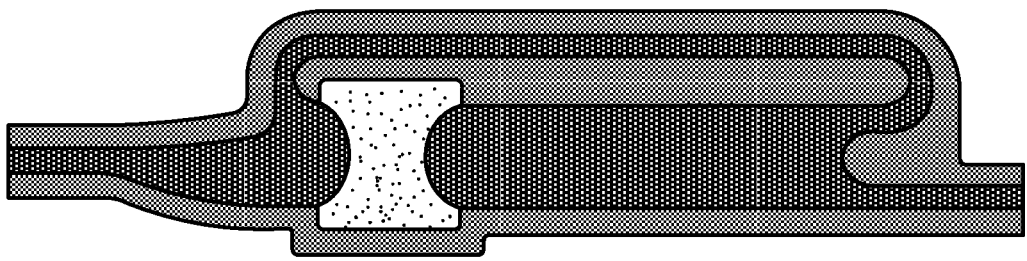

FIG. 4B shows blood filling the contaminant containment reservoir. If the air does not pass through the plug quickly enough, i.e. if the resistance through the plug is not lower than the resistance though the sample path, pressure will build up in the contaminant containment reservoir and force the fluid down the sample path prior to the contaminant containment reservoir filling with fluid. FIG. 4C shows a filled contaminant containment reservoir. Once all the air is pushed out of the contaminant containment reservoir (through the plug and sample path), fluid will hit the plug, and its progress through the plug is slowed and will possibly stop. This can force the fluid to flow down the sample path, leaving the initial volume of blood trapped in the contaminant containment reservoir. There might not be fluid flow through the plug at this point. FIG. 6 shows the fluid flow once the air is flushed from the device, an in particular from the contaminant containment reservoir. Subsequent blood volume will flow into and through the sample path, following the path of least resistance (lower pressure gradient) toward the distal end of the sample path and toward and out the outlet port.

Fluid flow can be completely stopped or allowed to flow slowly into the plug—it just cannot reach the other side and mix with the sample path during use.

Making the resistance of the air flow through the plug lower than through the sample path can be achieved by: 1) Cross sectional area—if the area of the plug is much larger than the area of the sample path, the resistance will be lower; and 2) Lengthening the sample path will increase the resistance, but the effect is much lower with air flow than with fluid flow.

The first amount of fluid can fill the contaminant containment reservoir first based on geometry—as shown in FIGS. 4A-4D, the inertia of the fluid will urge the fluid to keep it traveling straight into the contaminant containment reservoir rather than turning the corner into the sample path. In some implementations, the contaminant containment reservoir and the sample path, or any inlets and outlets thereof, can be coated differently to provide more or less resistance to fluid flow. For instance, coating the walls of the contaminant containment reservoir with a hydrophilic coating and the walls (or at least the entrance) of the sample path with a hydrophobic coating can help fill the contaminant containment reservoir first. The hydrophilic coating can include one or more of Polyurethane (PU), Polyvinylpyrolidone (PVP), Polyacrylic acid (PAA), and/or Polyethylene oxide (PEO). The hydrophobic coating can include Polytetrafluoroethylene (PTFE). Resistance in the sampling path may also be increased by inserting a dissolvable bio-compatible material in the path that dissolves upon contact with blood or a fluid, reducing the resistance to flow through the sample path once the contaminant containment reservoir is filled with fluid.

In another implementation, a benign, inert or non-reactive bio-compatible material, i.e., one that does not affect blood test results, can be placed in the device, or at least the junction to the contaminant containment reservoir, to block the sampling path. This material can be configured to dissolve when blood or fluid makes contact. Such material can be sized and configured to inhibit blood flow for a fraction of a second as the contaminant containment reservoir will fill almost instantaneously.

Figure 5:
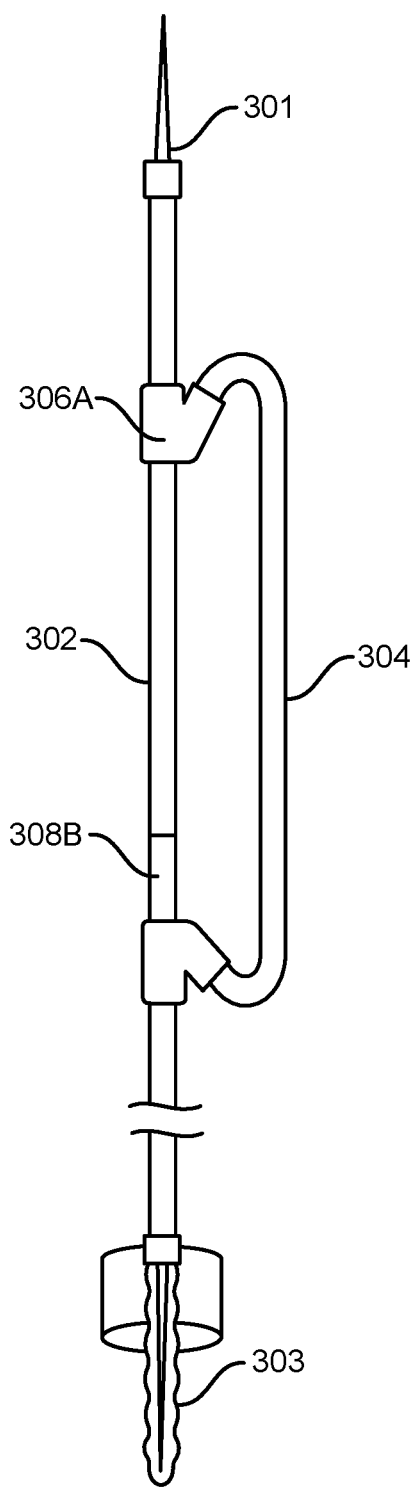
FIG. 5 shows a fluid sample optimization device without a housing.

FIG. 5 illustrates a housing-less implementation of a fluid sample optimization device 300 having a contaminant containment reservoir 302 and sample path 304 that are formed of tubing or other type of fluidic conveyance mechanism, and which form parallel or similar-directional paths via Y-site connectors 306A and 306B on opposite ends of the device. The Y-site connectors 306A and 306b can be provided in any orientation or alignment, and can be spaced apart sufficient to provide the contaminant containment reservoir 302, if implemented as tubing with a known cross-sectional diameter and length, with a predetermined volume. The contaminant containment reservoir 302 includes an air permeable fluid resistor 308 that is resistant to fluid flow but allows passage of air, so that, after a first amount or aliquot of fluid fills the contaminant containment reservoir 302, subsequent amounts of fluid bypass the contaminant containment reservoir 302 and flow through the sample path 304 for eventual collection by a fluid collection device.

A system employing the fluid sample optimization device 300 can include a patient needle 301 connected with the Y-site connector 306A, and a sample collection device 303 having a sealed sampling needle connected with the Y-site connector 306B. The tubing of the fluid sample optimization device 300 can be flexible or rigid. At least parts of the tubing can be made of a translucent material, so that a clinician can view a flow of blood therein. The fluid sample optimization device 300 can include a filter 308, which can be formed at least in part from air permeable blood resistor material. The filter 308 allows air in the contaminant containment reservoir 302 to be displaced therefrom through the filter 308 upon a vacuum force, or other mechanism creating a negative pressure differential between the sample collection device 303 and the In some implementations, a fluid sample optimization device 300 may function as a flash chamber, in which, upon venipuncture of a patient, blood may "flash" or be suddenly present in at least a portion of the contaminant containment reservoir 302, based at least in part on a vacuum force at an outlet junction of the fluid sample optimization device 300. Vacuum pressure draws the contaminated blood preferentially across the resistor (not capturing contaminated blood) into the contaminant chamber.

Figure 6A:
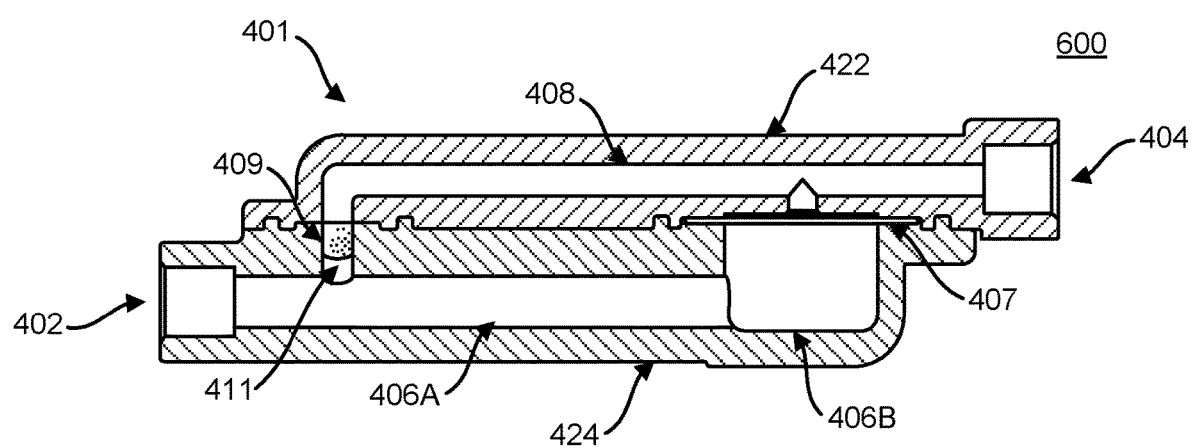

FIG. 6A shows a fluid sample optimization device 400 that includes an inlet 402 and an outlet 404. The inlet 402 can include an inlet port, connector or interface, for connecting to an external device such as tubing or interface thereof. The inlet 402 can be connected with a patient or a patient's fluid source, such as via a venipuncture needle, in which fluid is provided at pressure P1 and which can be the patient's own blood pressure. The outlet 404 can include an outlet port, connector or interface, for connecting to an external device such as tubing or an interface thereof. As discussed above, for instance, the outlet 404 can be connected with a fluid collection device, such as an evacuated tube like a Vacutainer® or a syringe, in which fluid is drawn by the fluid collection device from the fluid source by a pressure P2 that is lower than pressure P1. The pressure differential can allow the fluid sample optimization device 400 to be closed to atmosphere and atmospheric pressure, i.e. where the fluid sample optimization device 400 need not include any vent or pathway to outside atmosphere at least when in use.

The fluid sample optimization device 400 further includes a contaminant containment reservoir 406 connected with the inlet 402 and with the outlet 404, and having an air permeable fluid resistor 407 between a distal end of the contaminant containment reservoir 406 and the outlet 404. As further described herein, the contaminant containment reservoir 406 can be sized for holding a desired amount of fluid, and may contain an absorbent material that at least partially fills the contaminant containment reservoir 406. Also as further described herein, the contaminant containment reservoir 406 can be configured as a tortuous path, a series of chambers of differing cross sections and volumes, and/or contain rifling or baffles extending from an inner surface therein to minimize backflow, i.e. a flow toward the inlet 402. For instance, the contaminant containment reservoir 406 can include one or more channels 406A and one or more chambers 406B, all of which can be interconnected to receive, convey or contain a predetermined volume of fluid, as well as contain any contaminants therein.

The air permeable blood resistor 407 allows a first portion or amount of fluid to be drawn from the fluid source by a pressure differential applied between the inlet 402 and the outlet 404 to enter into the inlet 402 and into the contaminant containment reservoir 406, displacing air therein, until the fluid contacts the air permeable fluid resistor 407 where the flow fluid into the contaminant containment reservoir 406 is at least partially stopped.

The fluid sample optimization device 400 further includes a sample path 408 also connected with the inlet 402 and the outlet 404. The sample path 408 includes a resistive plug 409 provided proximate the inlet 402. At the same time a pressure differential between the inlet 402 and the outlet 404 can draw the first portion or amount of fluid into the contaminant containment reservoir 406, the resistive plug 409 is configured to resist, inhibit, limit or prohibit a flow of the fluid into the sample path 408 until the first portion or amount of fluid has entered into the contaminant containment reservoir 406.

The fluid sample optimization device 400 can further include a housing 401, which can define one or more of the inlet 402, the outlet 404, the contaminant containment reservoir 406, the sample path 408, or possibly other components such as the air permeable fluid resistor 407 and the resistive plug 409. The housing 401 can be formed in one or more parts. For instance, as shown in the example in FIG. 6A, the housing 401 can include a top housing portion 422 mated with a bottom housing portion 424, and which can be mated and sealed together by sonic welding, thermal bonding, gluing, or the like.

As described herein, the resistive plug 409 is configured such that after the first portion or amount of fluid has entered into the contaminant containment reservoir 406, the resistive plug 409 will allow a second and/or subsequent portions or amounts of fluid to flow from the inlet 402 through the sample path 408 to the outlet 404, still under force of a pressure differential between inlet 402 and the outlet 404. The resistive plug 409 can be recessed in the sample path 408 away from the inlet 402, to allow for vacuum pressure to build up, and can also include a pilot hole or small capillary, aperture, iris, or the like, to allow the dissolvable material to initiate being dissolved by fluid that continues to be drawn toward the outlet 404. Accordingly, a portion of the sample path 408 the inlet 402, and/or contaminant containment reservoir 406 can form a junction 411 proximate the resistive plug 409 and opposite a main portion of the sample path 408, to allow vacuum pressure to build up for better fluid access through the resistive plug 409 after the contaminant containment reservoir 406 is filled.

Once the fluid fills the contaminant containment reservoir 406, a volume of air can be trapped in the junction 411 between the fluid and the resistive plug 409. Without a way for air to escape, the fluid will not reach the dissolvable material that forms at least part of the resistive plug 409 to be able to flow down the sample path 406. Thus, as shown in FIGS. 6B-6I, an air path through or around the resistive plug 409 can be provided that will only allow air to flow once it is exposed to the full vacuum pressure of the collection device, as fluid fills the contaminant containment reservoir 406 and plugs the air-permeable fluid resistor 407, such that fluid does not come in contact with the dissolvable material in the resistive plug 409 until after the contaminant containment reservoir 406 is completely filled and/or the contaminants are contained therein.

FIG. 6B shows a variation of resistive plug 409 as a film 431, which can be formed as a thin film of material. In some implementations, the film 431 can be formed at least in part by a dissolvable or easily-torn material. The film 431 has a small orifice 432 or pilot hole as a mechanism to start the dissolving or tearing process. FIG. 6C shows a film 431 having a slit 433 that is closed in a static, steady state, but which can open and allow fluid flow when a pressure is applied to one or both opposite sides or surface of the resistor. In some implementations, as shown in FIG. 6D, the slit 433 can be formed as an "X" or other configuration, such as a linear slit, curved slit, star slit or the like. As shown in FIG. 6E, the film 431 can be formed as a porous membrane that allows air to flow through, but not bodily fluids such as blood. As shown in FIG. 6F, the film 431 can be positioned between the top housing portion 422 and the bottom housing portion 424 at the entrance to the sample path 408, so as to allow air to "leak" around the film 431 when a predetermined pressure is applied to it.

Figure 6G:
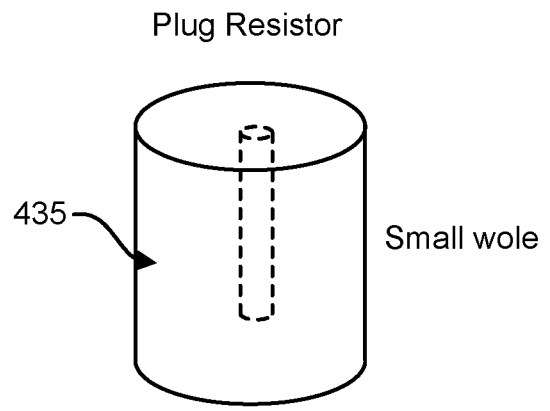
Figure 6H:
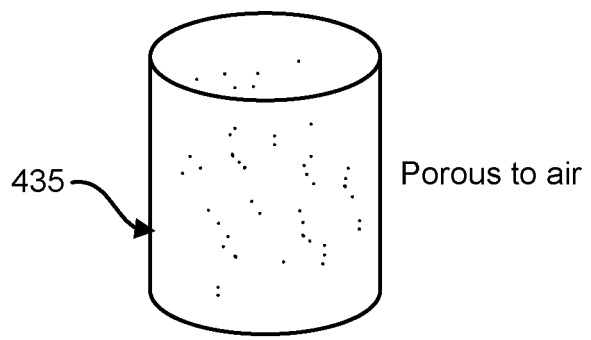
Figure 6I:
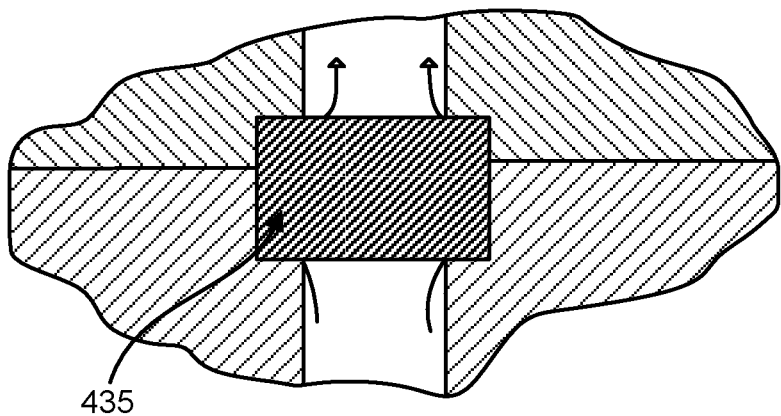

FIGS. 6G-6I illustrate a resistive plug 409 as a cylindrical plug member 435, although the resistive plug 409 can be formed in other shapes such as squared, rectangular, or other shape. The cylindrical plug member 435 can be provided with a small pilot hole, as shown in FIG. 6G, or be porous to air, as shown in FIG. 6H. The resistive plug 409, whether implemented as a cylindrical plug member 435 or other shape, can be positioned between the top housing portion 422 and the bottom housing portion 424 at the entrance to the sample path 408, so as to allow air to "leak" around the cylindrical plug member 435 when a predetermined pressure is applied to it.

Figure 7A:
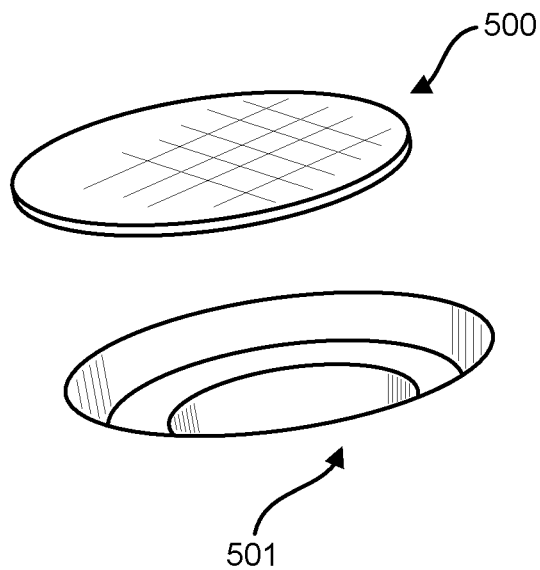
FIGS. 7A and 7B illustrate still other implementations of a resistor having a dissolvable material.
Figure 7B:
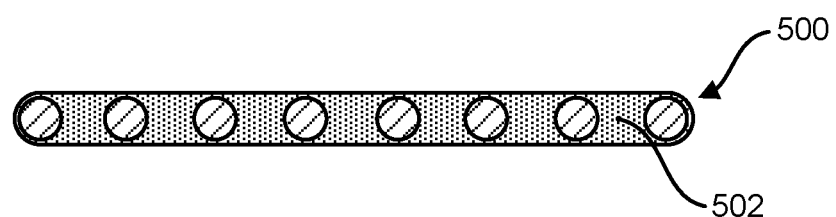

As further described herein and as shown in FIG. 7, a resistive plug 500 for an opening to the sample path can be formed of a composition that includes at least portion of a mesh 502 impregnated with a dissolvable material 504. In some specific implementations, the resistive plug 500 can include a mesh material that supports a dissolvable material 502. The mesh material can be, for example, a mesh of plastic or nylon, such as a mesh of 50-100 µm nylon or plastic thread. The dissolvable material 504, which may not be formable as a rigid plug or film, can be impregnated into the mesh 502 or other porous material. The dissolvable material 504 is dissolvable by contact with fluid, such as blood. The dissolvable material 504 is formulated to be inert or non-reactive to lab tests of sampled or collected fluid specimens, which are often provided with cultures to test for specific bacteria or viruses, or antibodies thereof, or other pathogens existing in the fluid sample.

Figure 8A:
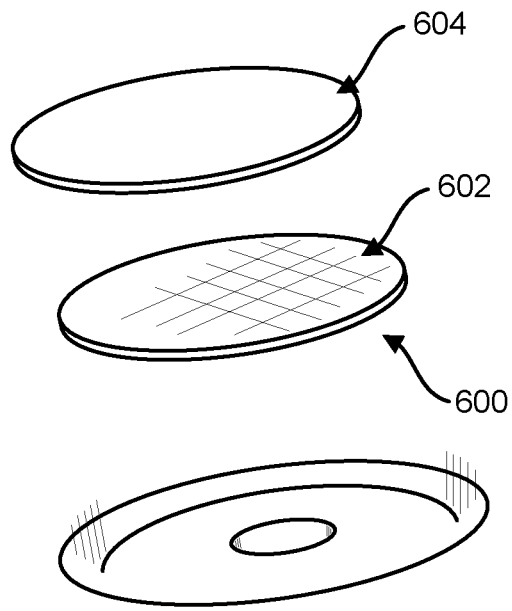
FIGS. 8A and 8B illustrate yet other implementations of a resistor having both a dissolvable material and a non-dissolvable material that is highly viscous.
Figure 8B:
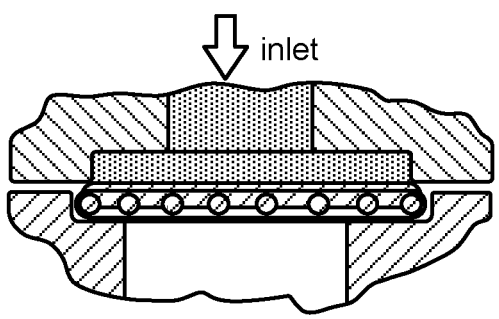
Figure 8B:
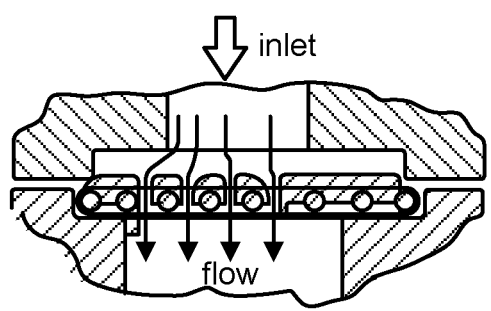

As shown in FIG. 8, a resistive plug 600 can also be formed of a mesh 602 as described above, but which is overlaid with, or integrates, a non-dissolvable viscous material 604, such as silicone grease. The viscous material 604 can be spread on the mesh 602 or other porous material. Once the pressure differential across the resistive plug 600 is high enough, the viscous material 604 is pulled through openings in the mesh 602 to create openings for the fluid sample to flow through, as shown in FIG. 8B. At most, only trace amounts of the viscous material 604 would ever exit the outlet, and therefore should not interfere with any testing or culturing of the fluid sample.

As shown in FIGS. 9A-9C, a resistive plug 700 can be formed of a membrane 702 stretched or positioned over and spaced apart from a piercing member 704 in an initial state. The piercing member 704 can include a spike, pin, blade, shard, or the like, and can be held substantially in the center of the opening to the sampling path, as shown in FIG. 9A, by a holding mechanism as shown in FIG. 9B. The membrane 702 can be an elastic sheet of material, such as a rubber or other elastomeric material. As shown in FIG. 9C, once the contaminant containment reservoir fills with fluid, an amount of pressure is exerted against the membrane 702 to stretch it further to contact the piercing member 704. Once contact is made between the membrane 702 and the piercing member 704, the membrane 702 is punctured or otherwise broken by the piercing member 704 to open a larger area for subsequent amounts or portions of fluid to flow into the sample path.

Figure 10B:
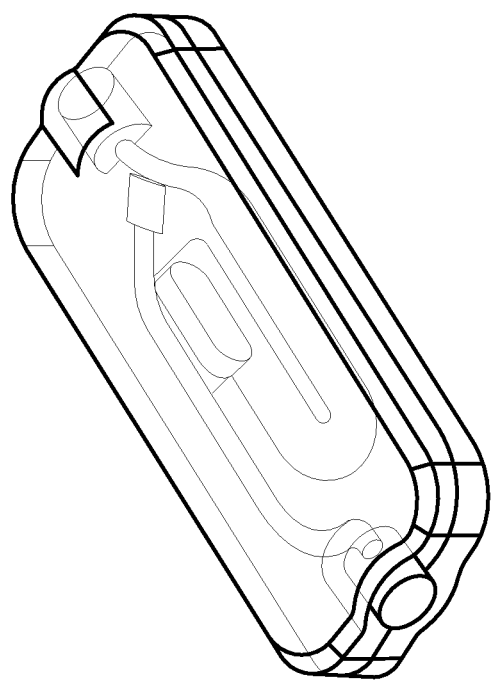
FIGS. 10A and 10B show a specific configuration of a non-venting fluid sample optimization device formed in a housing, using an elongated air permeable fluid resistor.
Figure 10A:
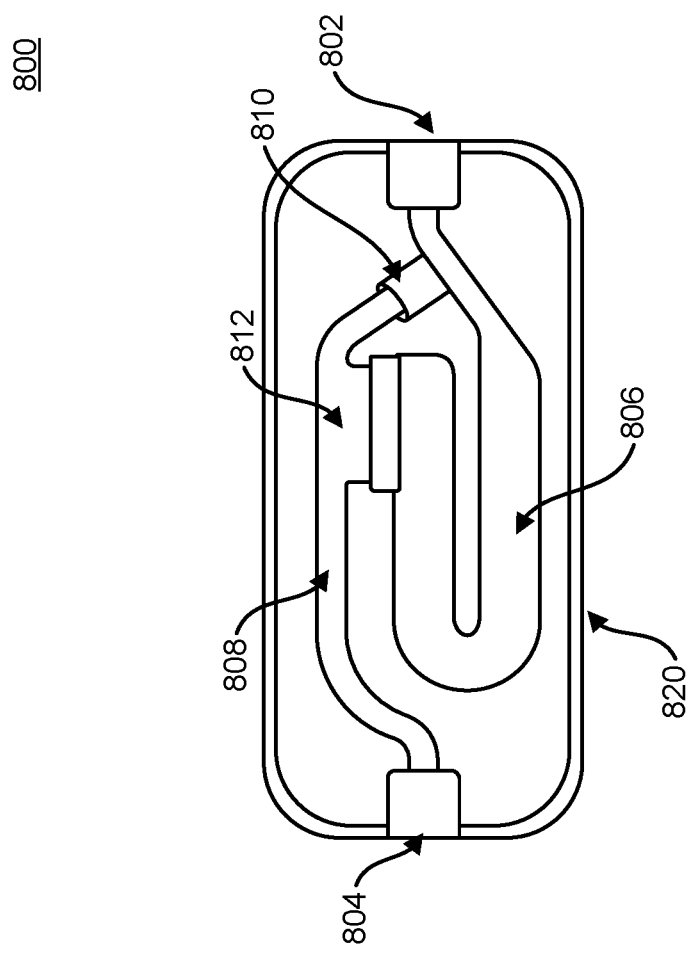

FIGS. 10A-11B show various views of a fluid sample optimization device 800 and 900 for optimizing a fluid sample collected by a fluid collection device from a fluid source, and where a first portion of the fluid sample potentially has contaminants. As shown in FIGS. 10A and 10B, a fluid sample optimization device 800 includes an inlet 802 configured to connect with the fluid source, an outlet 804 configured to connect with the fluid collection device, and a sample path 808 connected between the inlet 802 and the outlet 804. The fluid sample optimization device 800 further includes a contaminant containment reservoir 806 connected between the inlet 802 and the outlet 804. One or more of the inlet 802, outlet 804, contaminant containment reservoir 806 and sample path 808, and possibly other components of the fluid sample optimization device 800 can be housed in and/or defined by a housing 820.

Figure 12A:
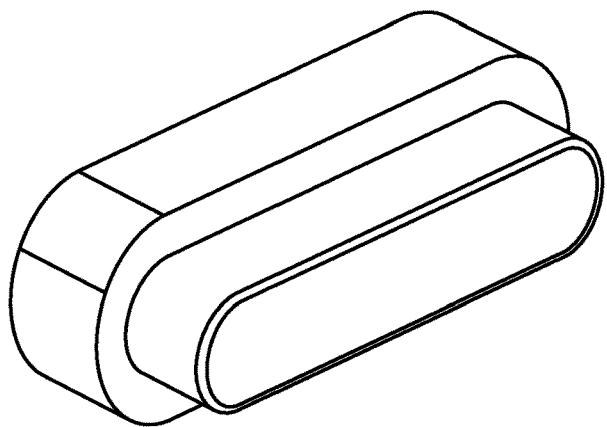
FIGS. 12A-12C show various configurations of an air permeable fluid resistor for use in implementations described herein.

The contaminant containment reservoir 806 further includes an air permeable fluid resistor 812 connected with the sample path 808, preferably proximate the outlet 804. The contaminant containment reservoir 806 is arranged to receive, when a pressure differential is applied between the inlet 802 and the outlet 804, a first portion of the fluid sample from the fluid source to displace air therein through the air permeable fluid resistor 812 and the outlet 804. The air permeable fluid resistor 812 can be elongated and configured for a particular air flow range, as shown in FIG. 12A, and can be self-sealing upon contact with non-air fluid such as blood or other bodily fluids.

Upon receipt of the first portion of the fluid sample and containment of the contaminants in the contaminant containment reservoir 806, subsequent portions of the fluid sample can be received and conveyed by the sample path 808 from the inlet 802 to the outlet 804 when subsequent pressure differentials are applied between the inlet 802 and the outlet 804. In some implementations, the fluid sample optimization device 800 includes a resistive plug 810 that initially substantially plugs the sample path 808 from the inlet 802 while, and until, the first portion of the fluid is received in the contaminant containment reservoir 806.

Figure 11B:
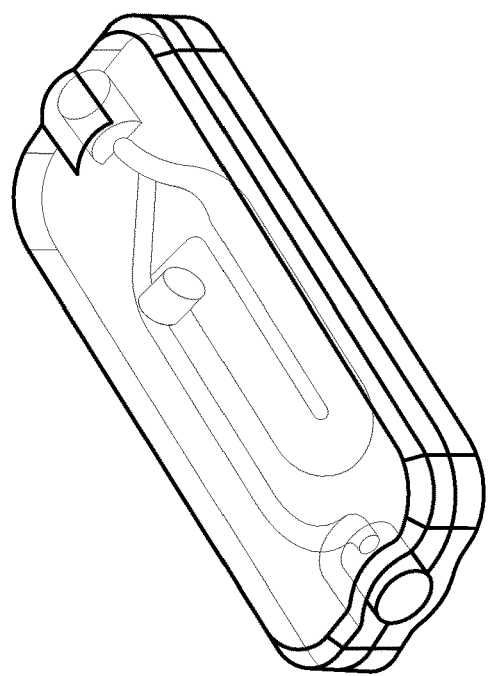
FIGS. 11A and 11B show another specific configuration of a non-venting fluid sample optimization device formed in a housing.
Figure 11A:
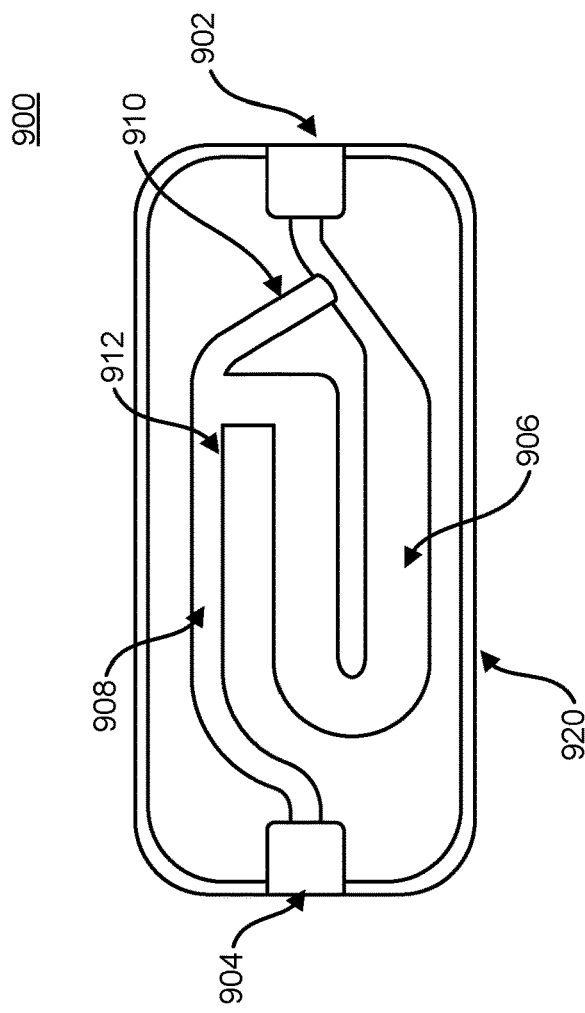

As shown in FIGS. 11A and 11B, a fluid sample optimization device 900 includes an inlet 902 configured to connect with the fluid source, an outlet 904 configured to connect with the fluid collection device, and a sample path 908 connected between the inlet 902 and the outlet 904. The fluid sample optimization device 900 further includes a contaminant containment reservoir 906 connected between the inlet 902 and the outlet 904. One or more of the inlet 902, outlet 904, contaminant containment reservoir 906 and sample path 908, and possibly other components of the fluid sample optimization device 900 can be housed in and/or defined by a housing 920.

Figure 12B:
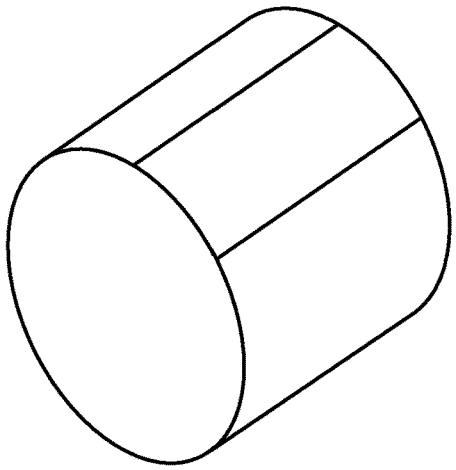
Figure 12C:
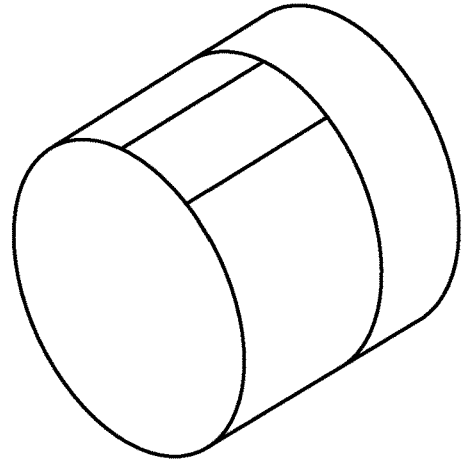

The contaminant containment reservoir 906 further includes an air permeable fluid resistor 912 connected with the sample path 908, preferably proximate the outlet 904. The contaminant containment reservoir 906 is arranged to receive, when a pressure differential is applied between the inlet 902 and the outlet 904, a first portion of the fluid sample from the fluid source to displace air therein through the air permeable fluid resistor 912 and the outlet 904. The air permeable fluid resistor 912 can be cylindrical and configured for a particular air flow range, and can be multi-layered to include a self-sealing layer that seals upon contact with non-air fluid such as blood or other bodily fluids, as shown in FIGS. 12B and 12C, respectively.

Upon receipt of the first portion of the fluid sample and containment of the contaminants in the contaminant containment reservoir 906, subsequent portions of the fluid sample can be received and conveyed by the sample path 908 from the inlet 902 to the outlet 904 when subsequent pressure differentials are applied between the inlet 902 and the outlet 904. In some implementations, the fluid sample optimization device 900 includes a resistive plug 910 that initially substantially plugs the sample path 908 from the inlet 902 while, and until, the first portion of the fluid is received in the contaminant containment reservoir 906.

Figure 13A:
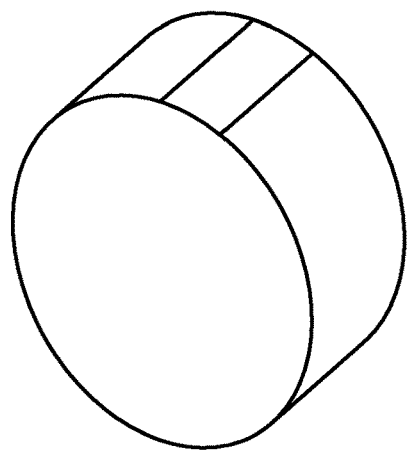
FIGS. 13A-13C show various configurations of a resistive plug for use in implementations described herein.
Figure 13B:
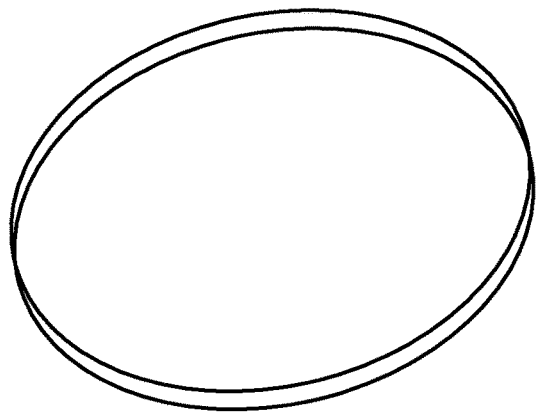
Figure 13C:
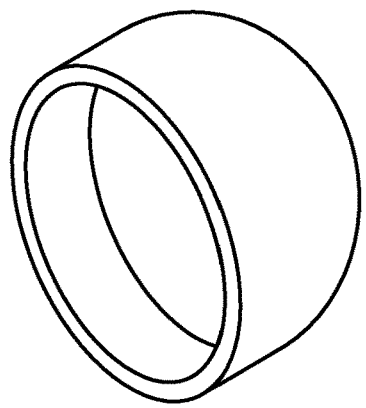

FIGS. 13A-13C show various implementations and configurations of a resistive plug, such as a cylindrical plug (FIG. 13A), a film or membrane (FIG. 13B), or a flexible cap (FIG. 13C).

Figure 14A:
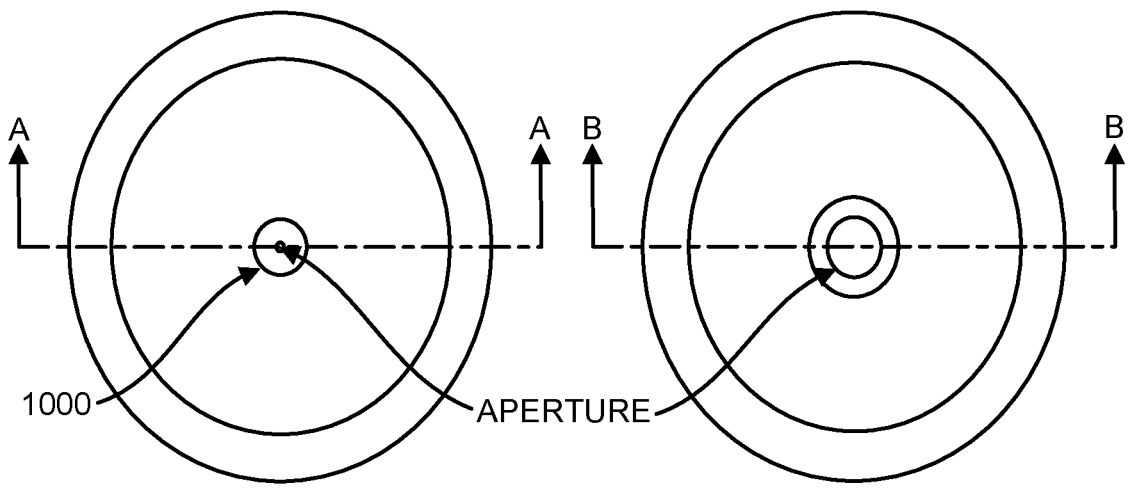
FIGS. 14A-14C illustrate a resistive plug having an iris or aperture that widens to open up upon certain pressure conditions.
Figure 14B:
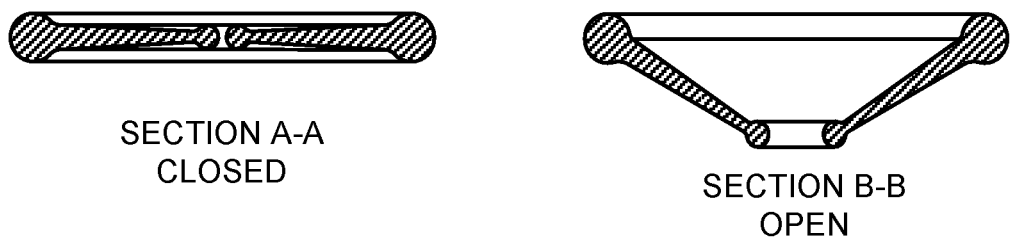
Figure 14C:
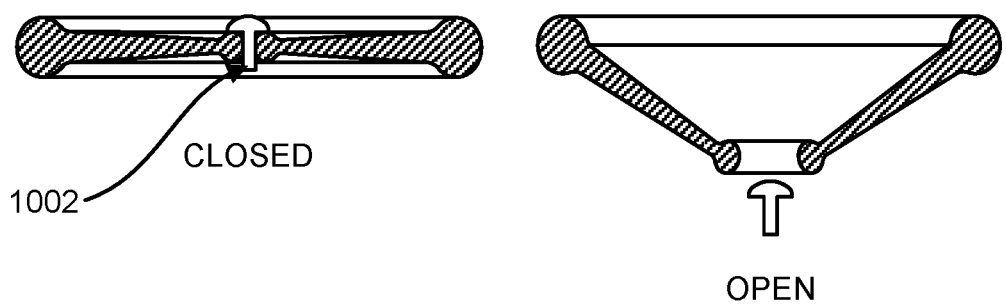

FIGS. 14A-14C illustrate a resistive plug with an aperture 1000 or iris that is selectively actuated/disrupted manually or automatically to allow or prevent flow through at different times and based on different pressures exerted on the resistive plug \. In some implementations, the resistive plug is an elastomeric membrane, with a small aperture 1000 substantially in the center. When a differential pressure is applied to one side of the membrane that forms the resistive plug, it will deflect and increase the size of the aperture 1000, allowing fluid to flow through to the output. Alternatively, the resistive plug can include a rigid or semi-rigid plug member 1002 that would cover the aperture 1000 and then fall out of the way once the aperture 1000 is activated.

Although a few embodiments have been described in detail above, other modifications are possible. Other embodiments may be within the scope of the following claims.

The invention claimed is:

1. A device for optimizing a fluid sample collected by a fluid collection device from a fluid source, the device comprising:
    an inlet configured to connect with the fluid source;
    an outlet configured to connect with the fluid collection device;
    a sample path connected between the inlet and the outlet, the sample path further having a resistive plug; and
    a chamber connected between the inlet and the outlet, the chamber having an air permeable fluid resistor proximate the outlet, the chamber being arranged to receive, when a pressure differential is applied between the inlet and the outlet, a first portion of the fluid sample from the fluid source to displace air therein through the air permeable fluid resistor and the outlet, such that upon receipt of the first portion of the fluid sample in the chamber, subsequent portions of the fluid sample can be conveyed by the sample path from the inlet to the outlet, the resistive plug including a membrane that is pierceable; and
    a piercing member configured to pierce the membrane, wherein the resistive plug and the piercing member are spaced apart from the chamber,
    wherein the device is configured such that, once the chamber fills with the first portion of the fluid sample, pressure is exerted against the membrane causing the membrane to stretch and contact the piercing member.

2. The device in accordance with claim 1, further comprising a housing that houses and/or defines one or more of the inlet, the outlet, the sample path, and the chamber.

3. The device in accordance with claim 1, wherein the air permeable fluid resistor includes a material that seals upon contact with the first portion of the fluid sample.

4. The device in accordance with claim 1, wherein the chamber includes a tortuous path.

5. A device for optimizing a fluid sample collected by a fluid collection device from a fluid source, the device comprising:
    an inlet configured to connect with the fluid source;
    an outlet configured to connect with the fluid collection device;
    a sample path connected between the inlet and the outlet, the sample path further having a resistive plug that is configured to inhibit at least a part of a first portion of the fluid sample from entering the sample path; and
    a chamber connected between the inlet and the outlet, the chamber further having an air permeable fluid resistor proximate the outlet, the chamber being arranged to receive, when a pressure differential is applied between the inlet and the outlet, the first portion of the fluid sample from the fluid source to displace air therein through the air permeable fluid resistor and the outlet, such that upon receipt of the first portion of the fluid sample in the chamber, subsequent portions of the fluid sample can be forced through the resistive plug and conveyed by the sample path from the inlet to the outlet, the resistive plug including a membrane that is pierceable; and a piercing member configured to pierce the membrane, wherein the resistive plug and the piercing member are spaced apart from the chamber, wherein the device is configured such that, once the chamber fills with the first portion of the fluid sample, pressure is exerted against the membrane causing the membrane to stretch and contact the piercing member.

6. The device in accordance with claim 5, further comprising a housing that houses and/or defines one or more of the inlet, the outlet, the sample path, and the chamber.

7. The device in accordance with claim 5, wherein the air permeable fluid resistor includes a material that seals upon contact with the first portion of the fluid sample.

8. The device in accordance with claim 5, wherein the chamber includes a tortuous path.

9. A device for optimizing a fluid sample, the device comprising:

an inlet;

an outlet;

a sample path connected between the inlet and the outlet; and a chamber connected between the inlet and the outlet, the chamber having an air permeable fluid resistor proximate the outlet, the chamber being arranged to receive, when a pressure differential is applied between the inlet and the outlet, a first portion of the fluid sample to displace air therein through the air permeable fluid resistor and the outlet, such that upon receipt of the first portion of the fluid sample in the chamber, subsequent portions of the fluid sample can be conveyed by the sample path from the inlet to the outlet, wherein the sample path further includes a resistive plug that is configured to inhibit at least a part of the first portion of the fluid sample from entering the sample path during receipt of the first portion of the fluid sample in the chamber, the resistive plug including a membrane that is pierceable; and a piercing member configured to pierce the membrane, wherein the resistive plug and the piercing member are spaced apart from the chamber, wherein the device is configured such that, once the chamber fills with the first portion of the fluid sample, pressure is exerted against the membrane causing the membrane to stretch and contact the piercing member.

10. The device in accordance with claim 9, further comprising a housing that houses and/or defines one or more of the inlet, the outlet, the sample path, and the chamber.

11. The device in accordance with claim 9, wherein the air permeable fluid resistor includes a material that seals upon contact with the first portion of the fluid sample.

12. The device in accordance with claim 9, wherein the chamber includes a tortuous path.

* * * * *